(12) United States Patent
Smith et al.

(10) Patent No.: US 8,303,982 B2
(45) Date of Patent: Nov. 6, 2012

(54) SELF-LOCATING, MULTIPLE APPLICATION, AND MULTIPLE LOCATION MEDICAL PATCH SYSTEMS AND METHODS THEREFOR

(75) Inventors: Daniel J. Smith, Dayton, NJ (US); Jessica Liberatore, Marlboro, NJ (US)

(73) Assignee: Ethicon, Inc, Somerville, NJ (US)

( * ) Notice: Subject to any disclaimer, the term of this patent is extended or adjusted under 35 U.S.C. 154(b) by 629 days.

(21) Appl. No.: 12/407,840

(22) Filed: Mar. 20, 2009

(65) Prior Publication Data

US 2010/0239648 A1    Sep. 23, 2010

(51) Int. Cl.
A61F 13/02    (2006.01)
A61F 13/00    (2006.01)
A61F 15/00    (2006.01)

(52) U.S. Cl. .......................................... 424/448; 602/54
(58) Field of Classification Search .......... 424/443–449; 602/54
See application file for complete search history.

(56) References Cited

U.S. PATENT DOCUMENTS

| | | | |
|---|---|---|---|
| 4,627,429 A | 12/1986 | Tsuk | |
| D296,006 S | 5/1988 | Asche | |
| 4,788,971 A | 12/1988 | Quisno | |
| 5,473,966 A * | 12/1995 | Cordon | 83/56 |
| 5,556,375 A | 9/1996 | Ewall | |
| 5,702,356 A * | 12/1997 | Hathman | 602/41 |
| 6,120,792 A | 9/2000 | Juni | |
| 6,344,021 B1 * | 2/2002 | Juster et al. | 600/15 |
| 6,572,636 B1 | 6/2003 | Hagen et al. | |
| 2002/0058893 A1 | 5/2002 | Vesey | |
| 2005/0277998 A1 | 12/2005 | Tracey et al. | |
| 2006/0195146 A1 | 8/2006 | Tracey et al. | |
| 2006/0195153 A1 | 8/2006 | Diubaldi et al. | |
| 2007/0071799 A1 | 3/2007 | Tacklind | |
| 2007/0185541 A1 | 8/2007 | Diubaldi et al. | |
| 2008/0038300 A1 | 2/2008 | Jaspers et al. | |
| 2008/0147146 A1 | 6/2008 | Wahlgren et al. | |

FOREIGN PATENT DOCUMENTS

WO    WO 02/098502 A2    12/2002

* cited by examiner

*Primary Examiner* — Fereydoun G Sajjadi
*Assistant Examiner* — Genevieve S Alley
(74) *Attorney, Agent, or Firm* — Cheryl F. Cohen, LLC

(57) ABSTRACT

A medical patch system has a first medical patch including an outer locating ring securable to a surface and an inner patch, separable from the outer locating ring, disposed within the outer locating ring. The medical patch system includes a second medical patch adapted for insertion into the central area bounded by the outer locating ring after the inner patch is separated from the outer locating ring. The second medical patch includes a second outer locating ring securable to the surface, and a second inner patch section, separable from the second outer locating ring, disposed within a second central area bounded by the second outer locating ring. The first and second outer locating rings have adhesive layers for securing the outer locating rings to a surface. The adhesive layers on the respective outer locating rings have different sizes, shapes or patterns to minimize skin irritation.

25 Claims, 15 Drawing Sheets

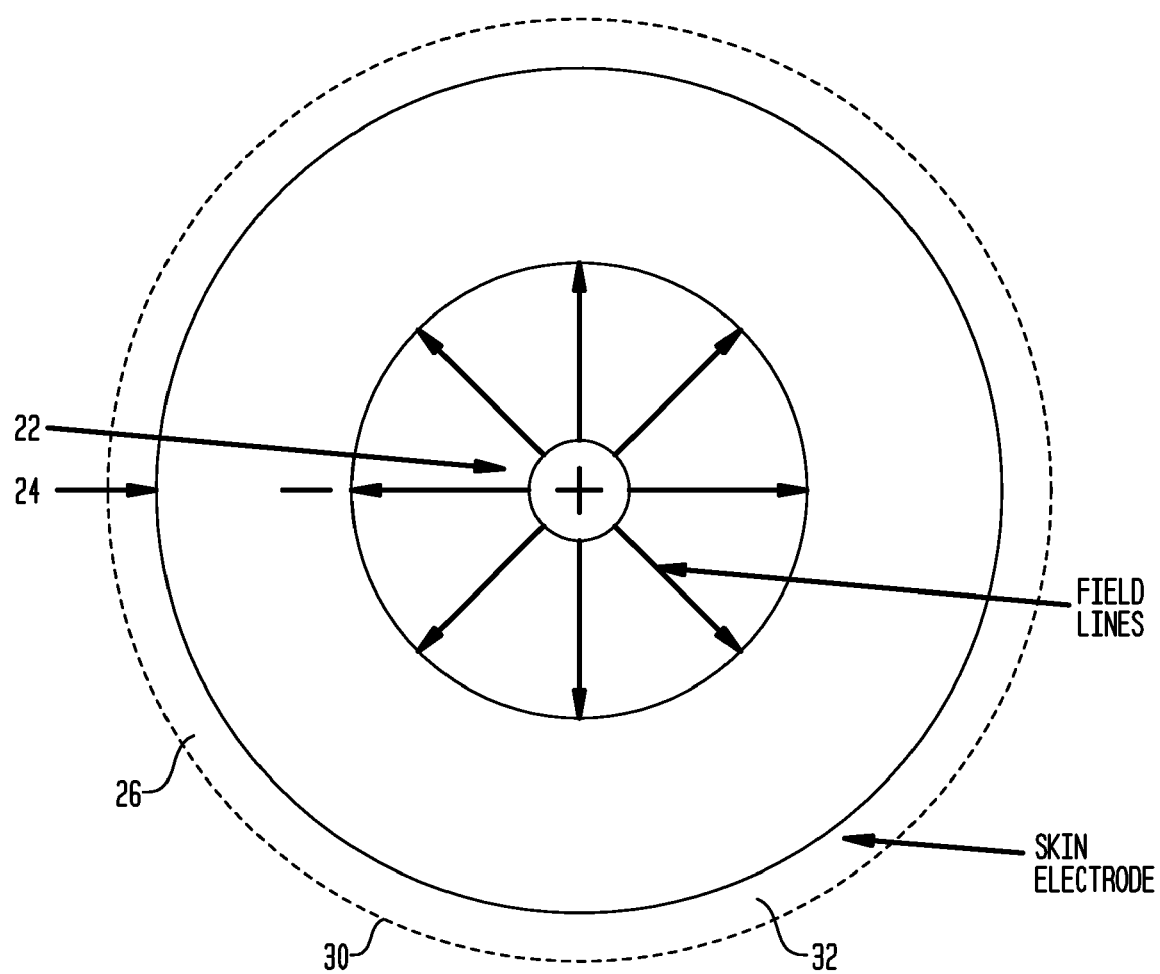

200

210

220

230

240

300

300

300

300

300

300

400

500

500

SELF-LOCATING, MULTIPLE APPLICATION, AND MULTIPLE LOCATION MEDICAL PATCH SYSTEMS AND METHODS THEREFOR

BACKGROUND OF THE INVENTION

1. Field of the Invention

The present invention generally relates to medical patches, and more specifically relates to medical patch systems and methods that enable patients to self-locate and apply a series of replacement medical patches.

2. Description of the Related Art

Medical delivery patches are generally used for nerve stimulation, and delivering pharmacological agents such as pain medication, drugs, and hormones. Medical patches are often adhered to a patient's skin surface with an operating portion of the patch directed toward a target location on the patient. Over a period of time, the medical patches deliver the nerve stimulation or the pharmacological agents to the patient for achieving a therapeutic benefit. In some instances, a series of medical patches are applied to the patient, whereby a first medical patch applied by a medical professional is removed from a patient's skin and replaced with a second medical patch. Eventually, the second medical patch may be removed and replaced by a third medical patch and so on. The application of the second medical patch is often done by the patient at home. Due to inexperience in properly placing replacement medical patches, the replacement medical patch may be improperly aligned over the target location on the patient, e.g. a particular nerve that is the target for nerve stimulation. In addition, medical patches are often adhered using adhesive layers. Skin irritation may occur if the adhesive layer on a second or subsequent patch contacts the same area of skin that was contacted by the adhesive layer from an earlier applied patch.

FIG. 1 shows a conventional medical patch 20, such as a medical patch used for neurostimulation, having a centrally located cathode 22 and a ring-shaped anode 24 that surrounds the cathode 22. The cathode 22 and the anode 24 are mounted on a support structure 26, such as a polyimide circuit, to form the concentric skin electrode patch 20. The medical patch 20 may be constructed from well-known electrode materials such as silver, silver/silver chloride, gold, titanium, or other conductive materials. The medical patch may also be made of conductive polymers, fibers and the like. The medical patch 20 may be a stand-alone component that is attached to a stimulation generator via a cable, as described in commonly owned U.S. patent application Ser. No. 11/146,522, the disclosure of which is hereby incorporated by reference herein. In instances where the medical patch 20 is incorporated into a flexible circuit, the flexible circuit may contain all of the required electronics required for generating stimulation signals. The flexible circuit may include mounting regions for receiving battery cells.

As shown in FIG. 1, the medical patch has an outer perimeter 30 and an adhesive layer 32 that extends around the outer perimeter 30. The adhesive layer 32 is used to attach the medical patch to a patient. In most instances, the adhesive layer 32 is placed in contact with the patient's skin for attaching the medical patch 20 to the patient. In many instances, after a period of time, it is necessary to remove the medical patch 20 and replace it with a second medical patch. If the replacement procedure is completed by the patient, and not medical personnel, the patient may not properly align the cathode 22 and the anode 24 over the target location on the patient's body. Even if the patient does properly position the medical patch on the skin, the adhesive layer 32 on the replacement patch is placed over the same location on the skin as the prior patch, which may cause skin irritation.

As is known to those skilled in the art, conventional medical patches such as those shown in FIG. 1 have one or more limitations. First, because the medical patches are affixed to the skin by means of adhesives, prolonged ambulatory use of these patches causes skin irritation due to the adhesives being affixed to the same location on the skin. Moreover, because the specific nerves to be stimulated can only be stimulated over a very small area, precise placement of the delivery patch is essential in order for the electrode to be therapeutic. Unfortunately, it is difficult for patients to perform precise placement of the replacement patches at home. Thus, better therapeutic results are obtained when using earlier placed medical patches than when using replacement medical patches.

In view of the foregoing, there is a need for a medical patch system and methods that provide for precise and repeatable placement of medical patches, whereby replacement medical patches are efficiently placed and aligned over a target location on a patient's body. Moreover, there is a need for medical patch systems and methods that cause minimal or no skin irritation during prolonged used. In addition, there is a need for medical patch systems and methods that enable patients to use tactile senses to identify the various parts of the patch, especially in instances where the patches are not visible to the user.

SUMMARY OF THE INVENTION

In one embodiment, a medical patch system addresses the alignment and location issues faced when using nerve stimulation patches. In one embodiment, the medical patch system provides a repeatable and accurate system for placing medical patches on a patient's body. The medical patch system also provides for continued adherence of the patch to the body for extended periods of time while minimizing localized skin irritation. In one embodiment, the medical patch system may be used for medical treatments other than nerve stimulation, such as drug delivery or pain management.

In one embodiment, a medical patch system enables frequent patch changes while maintaining location, which may provide for long-term adhesion of the patches to areas of the skin undergoing high stress or movement, or areas of the skin having elevated moisture levels.

In one embodiment, a medical patch system includes four medical patches that are each applied for about seven days for a total of 28 wear days. In one embodiment, a medical patch system includes six medical patches that are each applied for about five days for a total of 30 wear days. In one embodiment, the medical patches in a medical patch system are sequentially smaller. In another embodiment, the medical patches in a medical patch system are sequentially larger. In one embodiment, the medical patches in a medical patch system are sequentially smaller, and then reverse and are sequentially larger. The ability to use sequentially smaller patches and then reverse and use sequentially larger patches further enhances the ability to frequently change patches.

In one embodiment, a medical professional may position a first medical patch of a medical patch system over a target location on a patient's body. In one embodiment, the medical patch system is used for nerve stimulation and the first medical patch is positioned so that it stimulates a specific nerve or a nerve bundle at the target location on the patient's body. Each of the medical patches preferably has an active region that provides therapeutic benefit to the target location on the patient. In one embodiment, it is desirable to align the active regions of the respective medical patches with the target location on the patient for maximizing therapeutic benefit. As the medical patches are replaced, the active region of the replacement patch is preferably aligned with the target location on the patient. In one embodiment, aligning the active region of the replacement patch over the target location desirably includes using a part of an earlier-applied medical patch for aligning the replacement medical patch. In one embodiment, surgical alignment tools may be used for aligning the active regions of medical patches with target locations. The surgical alignment tools may use variables such as CMG measurements, pad tests, or measurements from landmarks. The alignment tools may also be used as a template to place or mark the patient for subsequent placement of medical patches. After the initial placement of the first medical patch by a medical professional, the self-locating and alignment features provided in the present invention enable patients to self-locate and apply additional and/or replacement patches at home for additional time periods without losing the target location on the patient's body. In one embodiment, the self-locating features preferably enable a patient to precisely locate at least one additional medical patch over the same target location.

In one embodiment, the self-locating patch concept offers a sequentially moving adhesive location to minimize skin irritation. The medical patch system desirably never leaves the adhesive portion of the patch in the same location for more than one time period. Thus, although the active regions of the replacement patches are aligned over the target location, the location of the adhesive on the replacement patches changes. In one embodiment, the patch locating feature may be applied in both a size descending and/or a size ascending manner for at least one additional patch, and can be applied in multiple locations, if necessary.

In one embodiment, a delivery patch system may include one or more patches having opposing tabs to remove either the outer locating ring or the inner patch section. The opposing tabs preferably provide the patient with tactile confirmation of the correct tab to pull, preferably for instances in which the patient cannot see the patch (e.g. the patch is covering a region of the patient's back). In one embodiment, the outer locating rings have peripheral tabs with tactile recesses and the inner patches have flexible flaps for identifying separation pull features.

The outer locating ring and the inner patch section may be detached from one another using a variety of structures such as a string pull tab, a molded tear off, or perforations. The detachment structure may protect the medical patch from moisture penetration depending upon application requirements.

In one embodiment, a medical professional may adjust the patch output or prescription, and the patch may have an up/down range within any given prescription setting. In one embodiment, a location on a body for the delivery patch is identified and the doctor then programs a series of patches to a patient's personal patch control unit. The patient then leaves the medical professional's office with a located patch, their personal patch control unit, and a series of patches to be used for a period of time. The patient may be required to return to the doctor who will assess the patient, reprogram and tune the personal patch controller as needed, and program any new patches, if necessary. This particular methodology allows both the patient and the doctor the ability to control and record patient history.

In one embodiment, a medical patch system includes a first medical patch having an outer locating ring secureable to a surface and an inner patch disposed within a central area bounded by the outer locating ring, the inner patch being separable from the outer locating ring. The medical patch desirably includes a second medical patch adapted for insertion into the central area bounded by the outer locating ring after the inner patch is separated from the outer locating ring. The outer locating ring desirably includes an adhesive for securing the outer locating ring to a surface. In one embodiment, a medical patch includes an active region that is desirably adapted to deliver a therapeutic benefit such as neurostimulation, pain-management agents, hormones, or pharmacological agents to a target location on a patient.

In one embodiment, the second medical patch includes a second outer locating ring secureable to a surface, such as a skin surface, and a second inner patch section disposed within a second central area bounded by the second outer locating ring, the second inner patch being separable from the second outer locating ring. The outer locating ring of the first medical patch is preferably removable from the surface (e.g. a skin surface) after the second outer locating ring of the second medical patch is secured to the surface. In one embodiment, the first outer locating ring of the first medical patch desirably includes an alignment surface for guiding alignment and orientation of the second medical patch relative to the first outer locating ring. The second outer locating ring preferably includes a second adhesive, such as an adhesive layer, for securing the second outer locating ring to the skin surface.

In one embodiment, each of the medical patches has an adhesive, preferably an adhesive layer, provided on the outer locating ring of the particular medical patch. The adhesives on the different medical patches preferably have a different size, shape or pattern from one another so that the adhesives do not cover the same location on the skin surface for avoiding skin irritation. The medical patches preferably replace one another over a target location on a patient. Altering the size, shape, or pattern of the adhesive for replacement medical patches desirably minimizes the likelihood of skin irritation because the adhesive of the replacement medical patch does not preferably cover the same location on the skin as the adhesive of the earlier-applied medical patch.

In one embodiment, the medical patch system includes a third medical patch adapted for insertion into the second central area bounded by the second outer locating ring after the second inner patch is separated from the second outer locating ring. In one embodiment, the second outer locating ring of the second medical patch includes an alignment surface for guiding alignment and orientation of the third medical patch relative to the second outer locating ring. The third medical patch may include a third outer locating ring secureable to the surface, and a third inner patch section disposed within a third central area bounded by the second outer locating ring, the third inner patch being separable from the third outer locating ring. The third outer locating ring preferably includes a third adhesive for securing the third outer locating ring to the surface.

In one embodiment, the outer locating ring of the second medical patch is removable from the surface after the third outer locating ring is secured to the surface. The second outer locating ring of the second medical patch includes an alignment surface for guiding alignment and positioning of the third medical patch relative to the second outer locating ring.

In one embodiment, each of the outer locating rings have alignment structure incorporated therein for ensuring precise alignment of active regions of the medical patches over the target location. In one embodiment, the alignment structure includes at least one magnet coupled with each of the outer locating rings. The magnets desirably generate a magnetic force that urges precise alignment of the outer locating rings relative to one another.

In one embodiment, the outer locating rings have irregular shapes that enable the outer locating rings to be assembled together in only one configuration. In one embodiment, the outer locating rings have a guitar shape with a larger diameter first end and a smaller diameter second end that ensures that the outer locating rings may be assembled together in only one configuration.

In one embodiment, at least one of the medical patches has at least one tactile identifier incorporated therein for distinguishing the medical patches from one another, or for identifying different part of one of the medical patches. In one embodiment, a tactile identifier includes a centrally located flexible flap over an inner patch. The flexible patch is desirably connected to a release extending between the inner patch and the outer locating ring associated with the medical patch. If the medical patch is not visually observable by the patient, the flexible flap may be identified by a patient using tactile senses.

In one embodiment, at least one tactile identifier includes a ledge extending outwardly from an outer edge of at least one of the outer locating rings. In one embodiment, a second medical patch is inserted into a central area bounded by the first outer locating ring and a first ledge on the first outer locating ring is offset from a second ledge on a second outer locating ring.

In one embodiment, a medical patch system includes at least two medical patches adapted to be secured in series over a target location. The at least two medical patches include a first medical patch having an outer alignment part and an inner part bounded by the outer alignment part. The inner part preferably has an active region that delivers a therapeutic benefit to the target location. The inner part is preferably separable from the outer alignment part for being replaced by a second medical patch. In one embodiment, the second medical patch is securable over the target location after the inner part of the first patch has been separated from the outer alignment part of the first medical patch for delivering a therapeutic benefit to the target location. The alignment and positioning of the second medical patch over the target location is preferably guided by the outer alignment part of the first medical patch.

In one embodiment, the second medical patch includes a second outer alignment part, and a second inner part bounded by the second outer alignment part. The second inner part preferably includes an active region that delivers a therapeutic benefit to the target location. The first and second outer alignment parts preferably include adhesive, such as adhesive layers, for securing the first and second medical patches over the target location. The first and second adhesive layers preferably have different sizes, shapes or patterns. The system may include a third medical patch adapted for insertion into an area bounded by the second outer alignment part after the second inner part is separated from the second outer alignment part.

In one embodiment, the first and second outer alignment parts have irregular shapes that generally confirm to one another for ensuring alignment of the active region of the second inner part over the target location. In one embodiment, each of the outer alignment parts may include at least one magnet for guiding alignment of the outer alignment parts relative to one another.

In one embodiment, a medical patch system includes a plurality of replaceable medical patches adapted to be secured in series over a target location, such as over a target location on a patient's body, to provide therapeutic benefit to the target location. At least one of the medical patches preferably includes an alignment surface for guiding proper alignment and orientation of a replacement medical patch over the target location. Each of the medical patches desirably includes an adhesive for securing the patches to a skin surface, the adhesives on at least two of the medical patches having different sizes, shapes, or patterns. In one embodiment, each medical patch desirably includes an outer locating ring, and an inner patch separable from the outer locating ring, whereby each of the inner patches includes an active region adapted to generate a therapeutic benefit provided to a target location.

In one embodiment, the medical patches are smaller in series so that a first medical patch is replaceable by a smaller second medical patch. In turn, the second medical patch may be replaceable by an even smaller third medical patch and so on. In one embodiment, a smaller medical patch may be replaced by at least one larger medical patch. In one embodiment, a medical patch system may include a first group of medical patches that are progressively smaller, followed by at least one larger medical patch, followed by a second group of medical patch that are progressively smaller. Thus, the medical patches may be replaced by smaller medical patches and then the order may reverse so that the patches are replaced by larger medical patches. The order of using smaller replacement patches may be repeated one or more times.

In one embodiment, at least one of the medical patches has a first region that is more flexible and a second region that is less flexible. The first more flexible region may be thinner than the second less flexible region. In one embodiment, the first more flexible region is made of one or more materials having more flexibility and the second less flexible region is made of one or more materials having less flexibility. In one embodiment, the first more flexible region is made of a material such as foam that provides for flexibility in multiple planes. In one embodiment, one or more medical patches are placed over a skin surface at a lower end of a tibia. As the surface at the lower end of the tibia is uneven, the flexibility of the patch is required for ensuring that the patch remains adhered to the patient through various body movements.

In one embodiment, a medical patch system may incorporate magnets for properly aligning and positioning subsequently applied medical patches. In one embodiment, an outer locating ring of a first medical patch may have a positive magnet and a negative magnet, and a second medical patch may have a positive magnet and a negative magnet that interacts with the magnets in the outer locating ring to ensure proper alignment of the second medical patch relative to the outer locating ring. If a patch is not properly aligned, the magnets may repel one another to indicate improper alignment. If the second patch is oriented properly relative to the first outer locating ring, then the second patch will be attracted to and/or properly seated within the outer locating ring. The magnets are preferably incorporated into the medical patch parts, with no need to implant any magnets under the patient's skin.

In one embodiment, a method of treating a patient using a series of skin patches includes selecting a location on a patient for medical treatment, placing a medical patch on the patient for providing medical treatment at the location, removing a first section of the medical patch and leaving a second section of the medical patch on the patient, and using the second section of the medical patch that remains on the patient for guiding alignment and positioning of a second medical patch on the patient for providing medical treatment at the location. In one embodiment, the second medical patch is smaller than the first medical patch so that after the second medical patch has been positioned, the second medical patch preferably lies within an area vacated by the removed first section of the first medical patch. In one embodiment, the second medical patch is larger than the first medical patch and lies outside at least a portion of the first medical patch.

In one embodiment, magnets may be incorporated into the respective medical patches for generating magnetic fields used to guide alignment and positioning of replacement medical patches. In one embodiment, a medical patch system includes magnets coupled with medical patches for guiding precise alignment and positioning of replacement medical patches over a target location. In one embodiment, the magnets may be embedded within portions of the medical patches. In one embodiment, an outer locating ring of a first medical patch includes positively charged magnets incorporated into the respective ends of the outer locating ring, and negatively charged magnets incorporated into the respective sides of the outer locating ring. The medical patch system preferably includes a second medical patch that is adapted to be positioned within a central opening of the outer locating ring. The second medical patch includes negatively charged magnets incorporated into the respective ends thereof, and positively charged magnets incorporated into the respective sides thereof. As the second medical patch is inserted into the central opening of the outer locating ring, the oppositely charged magnets generate a magnetic attraction that guides alignment of the second medical patch relative to the outer locating ring of the first medical patch.

These and other preferred embodiments of the invention will be described in more detail below.

BRIEF DESCRIPTION OF THE DRAWING

FIG. 1 shows a conventional medical patch.

DETAILED DESCRIPTION

Figure 2A:
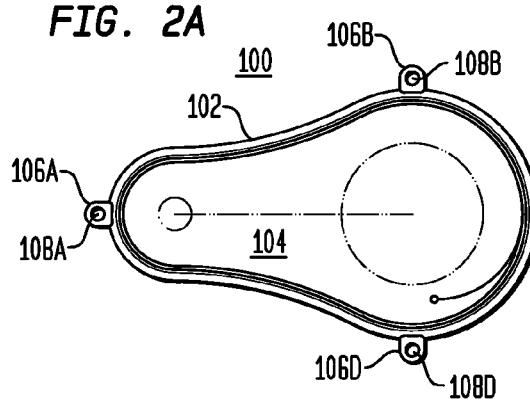
FIGS. 2A-2F show a system for aligning and positioning medical patches, in accordance with one embodiment of the present invention.

Referring to FIG. 2A, in one embodiment, a medical patch system includes a self-locating medical patch 100 having a first size. The medical patch 100 includes an outer locating ring 102 and an inner patch 104 that is connected with the outer locating ring 102. An underside surface of the outer locating ring 102 (i.e. the surface in contact with the skin), desirably has an adhesive provided thereon for adhering the outer locating ring 102 to the skin surface. The medical patch 100 may be used for a wide range of medical needs, including providing neurostimulation, delivering pain management pharmacological agents, and/or delivering other pharmacological agents not associated with pain management (e.g. hormones).

As will be described in more detail below, the medical patch system desirably includes two or more patches having different sizes. The medical patch system may include a series of patches that perform the same function, but that have different sizes. In one embodiment, the medical patches are sequentially smaller. In another embodiment, the medical patches are sequentially larger. In yet another embodiment, the medical patches are sequentially smaller, and then reverse to be sequentially larger.

Referring to FIG. 2A, the outer locating ring 102 preferably includes alignment features provided thereon. The outer locating ring 102 may also have structure for peeling the ring from a patient's skin. In the embodiment shown in FIG. 2A, the alignment features preferably include a series of alignment tabs 106A-106D that may be spaced from one another along the outer perimeter of the outer locating ring 102. Each of the alignment tabs 106A-106D desirably has a respective opening 108A-108B extending therethrough. Each of the respective openings 108A-108D is adapted to enable medical personnel and/or patients to align the outer locating ring 102 with one or more markers on a patient's body.

In one embodiment, a physician or medical personnel identify a location on a body where the medical patch 100 should be positioned for optimizing therapeutic benefit. The optimal location may be identified by placing markings, such as tattoos, on the skin of the patient. The markings may be placed by using the openings 108A-108D extending through the alignment tabs 106A-106D. In one embodiment, if the markings on the skin are observable through the openings 108A-108D in the alignment tabs 106A-106D, the first medical patch 100 has been properly positioned at the optimal location on the patient's body.

Figure 2B:
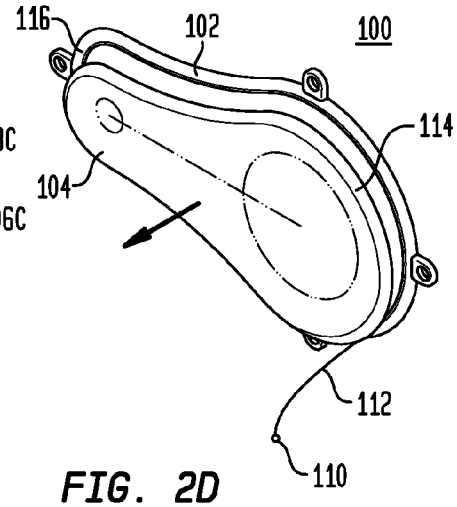

Referring to FIG. 2B, in one embodiment, the medical patch 100 includes a release tab 110 that may be pulled for separating the inner patch 104 from the outer locating ring 102. The release tab 110 preferably includes an elongated element 112, such as a flexible element or a string that extends between the outer edge 114 of the inner patch 104 and the inner edge 116 of the outer locating ring 102.

Figure 2C:
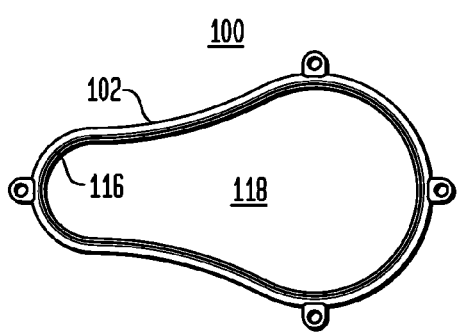

Referring to FIGS. 2B and 2C, after the release tab 110 is pulled, the inner patch 104 is separated from the outer locating ring 102. The inner patch 104 is removed, leaving the outer locating ring 102 attached to the patient's skin. The inner edge 116 of the outer locating ring 102 defines a boundary extending about a central opening 118 adapted to receive a second medical patch that has a smaller size (e.g. a smaller perimeter) than the first medical patch 100 shown and described in FIGS. 2A and 2B.

Figure 2D:
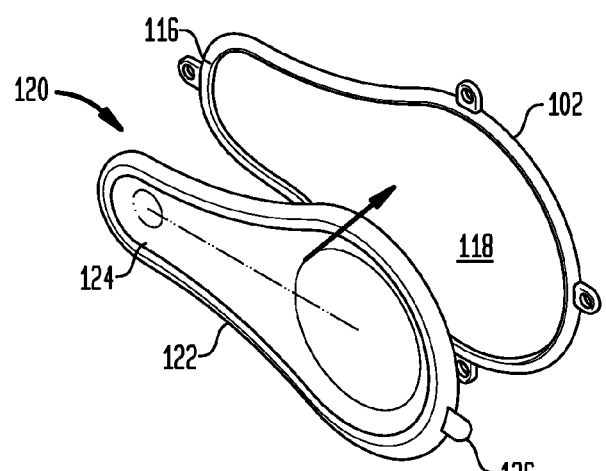

Referring to FIG. 2D, in one embodiment, a second medical patch 120 is positioned within the central opening 118 bounded by the inner edge 116 of the outer locating ring 102. The second delivery patch 120 includes a second outer locating ring 122 and a second inner patch 124 connected with the second outer locating ring 122. An underside surface of the second outer locating ring 122 of the second patch 120 desirably includes an adhesive for attaching the second medical patch 122 to a patient's skin surface. The second outer locating ring 122 preferably includes one or more tabs 126 that may be used for alignment and/or providing a mechanism for grasping the second outer locating ring 122. In one embodiment, the one or more tabs 126 may be used for peeling the second outer locating ring 122 from a patient's skin, as will be described in more detail below.

Referring to FIG. 2D, the second delivery patch 120 is preferably centered within the central opening 118 of the first outer locating ring 102. In one embodiment, the outer perimeter or outer edge of the second outer locating ring 122 desirably conforms to the inner edge 116 of the first outer locating ring 102 for ensuring proper alignment of the second medical patch 120 relative to the first outer locating ring 102. Proper alignment of the second medical patch 120 relative to the first outer locating ring 102 is highly preferred for maximizing continued therapeutic benefit. In one embodiment, placement of the second medical patch 120 may be done at home by the patient.

Figure 2E:
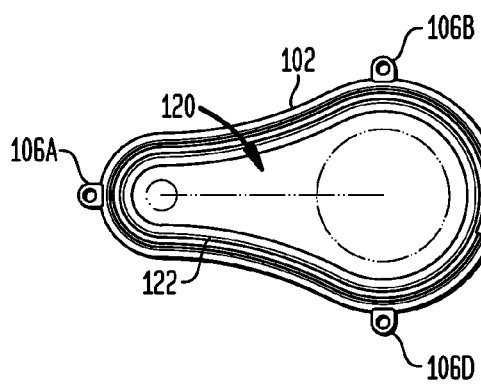

FIG. 2E shows the second medical patch 120, including the second outer locating ring 122 and the inner patch 124, after being positioned within the first outer locating ring 102. The adhesive on the underside of the second outer locating ring 122 is located inside the adhesive on the underside of the first outer locating ring 102, which minimizes the likelihood of skin irritation that results when adhesive is repeatedly placed in contact with the same patch of skin.

Figure 2F:
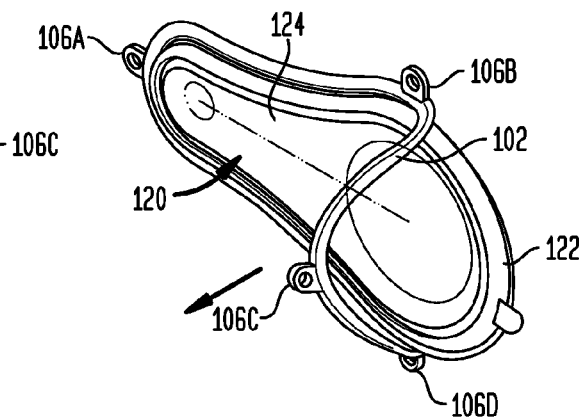

Referring to FIGS. 2E and 2F, in one embodiment, after the second medical patch 120 has been aligned within the first outer locating ring 102 and attached to the patient's skin, one or more of the alignment tabs 106A-106D on the first outer locating ring 102 may be pulled for removing the first outer locating ring 102 from the patient's skin. After the first outer locating ring 102 has been removed, the second medical patch 120 remains attached to the patient. Using the first outer locating ring 102 as an alignment guide preferably centers the second medical patch 120 over the optimal section of the patient's skin for maximizing therapeutic benefit. The adhesive on the underside surface of the second outer locating ring 122 is preferably adhered to a different section of the patient's skin, thereby minimizing skin irritation while ensuring proper adherence between the second medical patch 120 and the patient's skin.

Figure 3A:
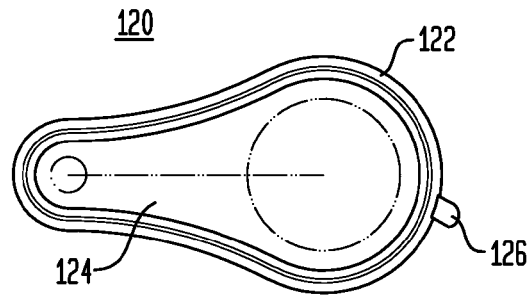
FIGS. 3A-3F show a system for aligning and positioning medical patches, in accordance with one embodiment of the present invention.

FIG. 3A shows the second medical patch 120 affixed to the patient's skin. In one embodiment, the second medical patch 120 preferably has a size and/or perimeter that is smaller than the first medical patch 100 (FIG. 2A). The second medical patch 120 includes the second locating ring 122 having the tab 126 and an inner patch 124 connected with the second outer locating ring 122. As noted above, an underside surface of the second outer locating ring 122 preferably has an adhesive for affixing the second medical patch 120 to the patient's skin.

Figure 3B:
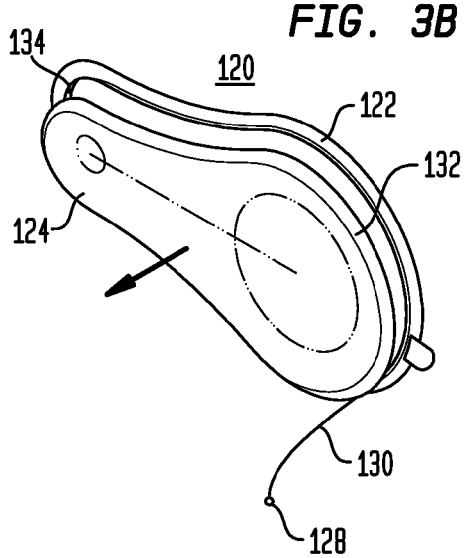

Referring to FIG. 3B, after a period of time (e.g. seven days), it may be desirable to remove the second medical patch 120 from the patient's skin and replace it with a smaller third medical patch (not shown). In one embodiment, the second medical patch 120 includes a release tab 128 connected to a flexible element 130 such as a string that extends between an outer edge 132 of the inner patch 124 and an inner edge 134 the second outer locating ring 122. The release tab 128 and the string 130 may be pulled for separating the inner patch 124 from the second outer locating ring 122. After the release tab 128 and the string 130 have been completely pulled, the second inner patch 124 may be separated from the second outer locating ring 122 that remains affixed to the patient's skin.

Figure 3C:
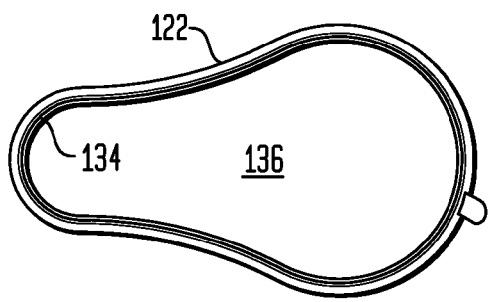

FIG. 3C shows the second outer locating ring 122 affixed to the patient's skin after the inner patch 124 has been removed. The second outer locating ring 122 includes the inner edge 134 that bounds and defines a central opening 136 of the second outer locating ring 122. The inner edge 134 of the second outer locating ring 122 may serve as an alignment guide for positioning a smaller, third medical patch within the central region 136 of the second outer locating ring 122.

Figure 3D:
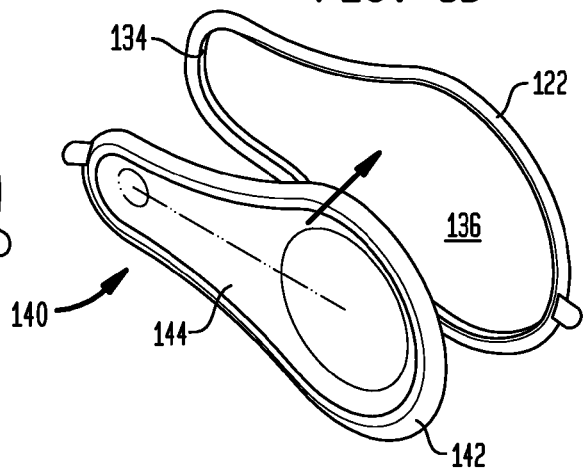

Referring to FIG. 3D, in one embodiment, a third medical patch 140 is preferably positioned within the central region 136 of the second outer locating ring 122. The third medical patch 140 preferably includes a third outer locating ring 142 and an inner patch 144 attached to the third outer locating ring 142. The third outer locating ring 142 preferably includes a tab 136 for, inter alia, peeling the third outer locating ring 142 from a patient's skin, if necessary.

Figure 3E:
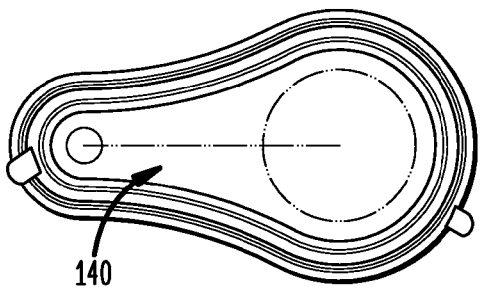

Referring to FIGS. 3D and 3E, the third medical patch 140 is seated within the central opening 136 defined by the inner edge 134 of the second outer locating ring 122. The inner edge 134 of the second outer locating ring 122 preferably serves as a guide for alignment of the third medical patch 140. An underside surface of the third outer locating ring 132 of the third medical patch 140 desirably includes an adhesive for adhering the third medical patch to a surface, such as a patient's skin surface.

Figure 3F:
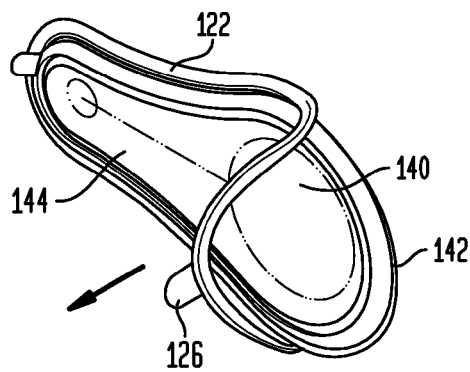

Referring to FIG. 3F, after the third medical patch 130 has been affixed within the central opening of the second outer locating ring 122, the release tab 126 may be pulled for peeling the second outer locating ring 122 from the patient's skin. After the second outer locating ring has been peeled away, the third medical patch 140 remains in place on the patient's skin. The third medical patch is preferably aligned over the optimum position on the patient's skin. The third medical patch includes the third outer locating ring 142 and the inner patch 144 connected the third outer locating ring 142. The third medical patch 130 is desirably smaller than the second medical patch 120 (FIG. 3A), which, in turn, is preferably smaller than the first medical patch 100 (FIG. 2A).

In FIGS. 2A-2G and 3A-3G, a series of three sequentially smaller delivery patches are shown. The delivery patches are sequentially smaller, inter alia, so that the adhesive materials used on the underside surfaces of the respective outer locating rings are aligned with different locations on the skin surface for minimizing skin irritation. The outer locating ring of a larger medical patch is used as a guide for aligning the subsequently positioned smaller medical patch to ensure that the subsequently positioned medical patch is positioned at an optimal location on the patient's skin for maximizing therapeutic benefit. Although the preferred system shown in FIGS. 2A-2G and 3A-3G includes three medical patches, other preferred systems may include fewer or more medical patches having varying sizes, such as a five or six patch system, whereby at least some of the medical patches have different sizes.

In one embodiment, a patch system includes two or more medical patches that are sequentially smaller so that skin irritation is avoided. In other embodiments, the size of the medical patches may first be smaller, and then reverse in a series of at least one larger patch. Although the present invention is not limited by any particular theory of operation, it is believed that adhering a series of medical patches to different regions of the skin, while maintaining alignment of the patch over the target location on the patient, maximizes therapeutic benefit while minimizing skin irritation.

Figure 4A:
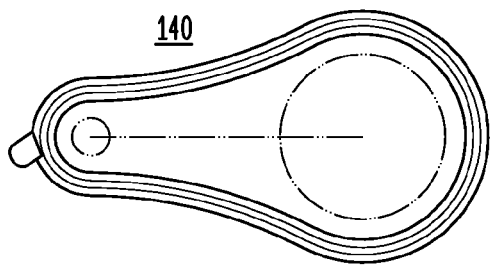
FIGS. 4A-4I show a system for aligning and positioning medical patches, in accordance with one embodiment of the present invention.

Referring to FIG. 4A, in one embodiment, the third medical patch 140 is adhered to the patient's skin. After a period of time, it may be desirable to remove the third medical patch 140 and replace it with another medical patch so as to continue treatment. In one embodiment, a template 150 is used for guiding alignment and placement of a fourth medical patch. The template 150 is preferably larger than the third medical patch 140. The template 150 preferably includes a fourth outer locating ring 152 and an inner section 154 having a central cutout 156 formed therein having a size and shape that closely conforms to the size and shape of the third medical patch 140.

Figure 4B:
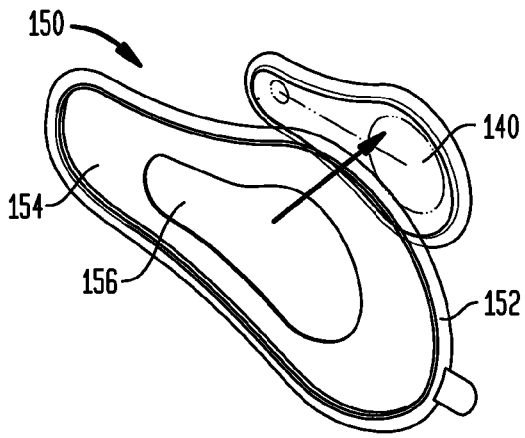
Figure 4C:
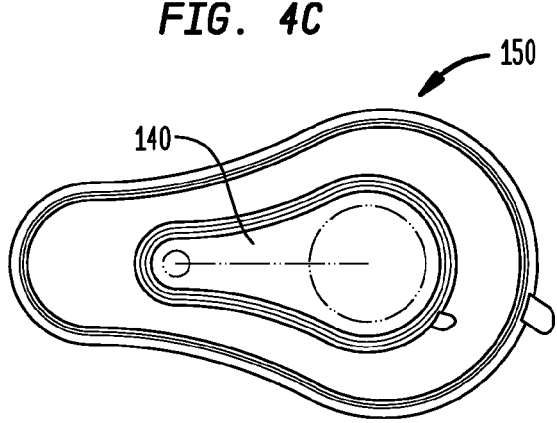

Referring to FIG. 4B, in one embodiment, the central cutout 156 of the template 140 is positioned over the outer perimeter of the third medical patch 130. The fourth outer locating ring 152 of the template 150 preferably includes an adhesive for adhering the fourth outer locating ring 152 of the template 150 to a patient's skin surface. FIG. 4C shows the template 150 after it has been aligned over the third medical patch 140.

Figure 4D:
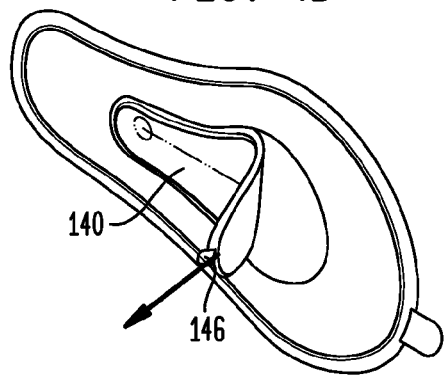
Figure 4E:
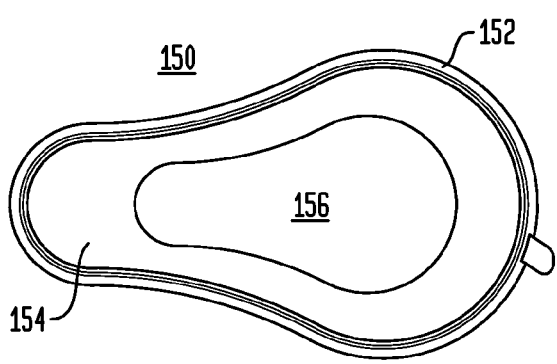

Referring to FIG. 4D, a release tab 146 on the third outer locating ring 132 of the third medical patch 140 may be pulled for peeling the third medical patch 140 away from the patient's skin surface. Referring to FIG. 4E, after the third medical patch 140 is removed, the template 150, including the fourth outer locating ring 152, the inner section 154, and the central cutout 156, remains adhered to a skin surface.

Figure 4F:
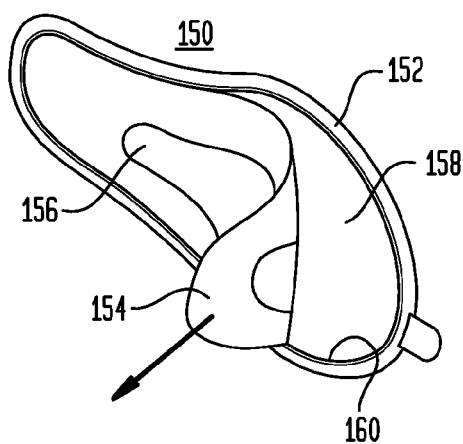
Figure 4G:
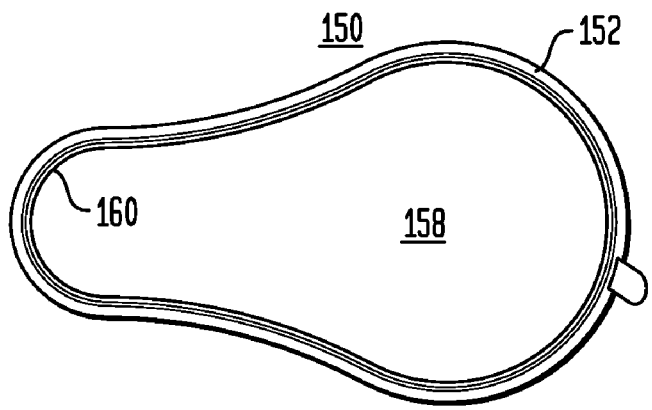

Referring to FIGS. 4F and 4G, in one embodiment, the inner section 154 of the template 150 is separated from the fourth outer locating ring 152 to provide a central alignment opening 158. The fourth outer locating ring 152 of the template 150 includes an inner edge 160 that provides an alignment surface for positioning an additional medical patch within the fourth outer locating ring 152.

Figure 4H:
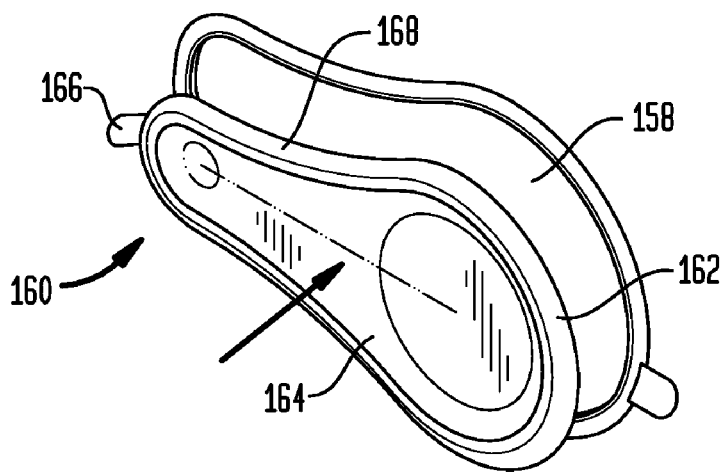
Figure 4I:
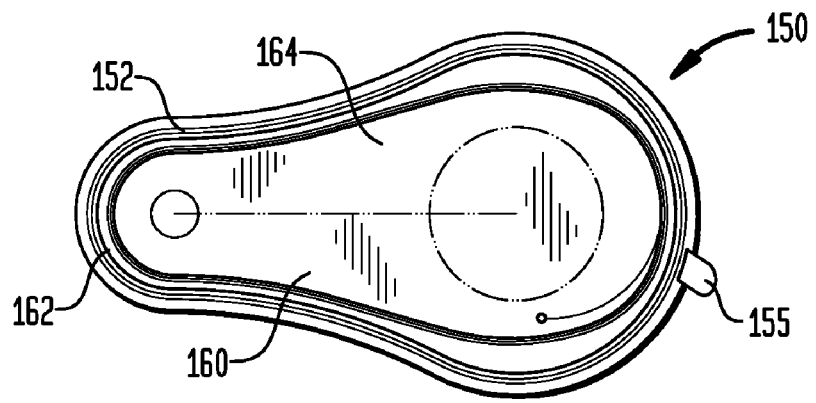

Referring to FIG. 4H, in one embodiment, a fourth medical patch 160 that is preferably larger than the third medical patch 140 (FIG. 4A) may be inserted into the central alignment opening 158. The fourth medical patch 160 preferably includes a fifth outer locating ring 162 that surrounds an inner patch 164. The fifth outer locating ring 162 desirably includes a release tab 166. An underside surface of the fifth outer locating ring 162 desirably includes an adhesive for adhering the larger fourth medical patch 160 to the patient's skin. FIG. 4I shows the fourth medical patch after it has been positioned within the outer locating ring 152 of the template 150. An outer edge 168 of the fifth outer locating ring 162 desirably engages the inner edge of the outer locating ring 152 of the template 150. A release tab 155 on the outer locating ring 152 of the template 150 may then be pulled for peeling the outer locating ring 152 from the patient's skin. After the outer locating ring 152 of the template 150 has been removed, the fourth medical patch 160 remains adhered to the patient's skin for providing a therapeutic benefit.

In one embodiment, a system of self-locating medical patches includes a series of medical patches having different sizes that are adapted to be positioned in sequence over a designated location on a patient. In one embodiment, a later deployed medical patch may be smaller in size than an earlier deployed medical patch. An outer locating ring of the larger patch may be used to align the smaller patch. This process can be repeated for aligning and positioning a series of smaller and smaller patches over a target location on a patient. In another embodiment, one or more of the medical patches may be larger in sequence.

In one embodiment, a medical patch system may include medical patches made of one or more of the following materials including polyimides, copper, gold, silver, silver ink, tin, polycarbonate, lithium ion, lithium polymer, silicon, thin metal sheets, thin metal films, urethanes, polyurethanes, polyurethane tephthalate urethane foams, foams, epoxies, adhesives, conductive adhesives, adhesive films, flexible films, breathable films, hydrogels, papers, wax papers, silicones, aluminum, anodized aluminum, Tyvek, and any combination of the above-listed materials.

Figure 5A:
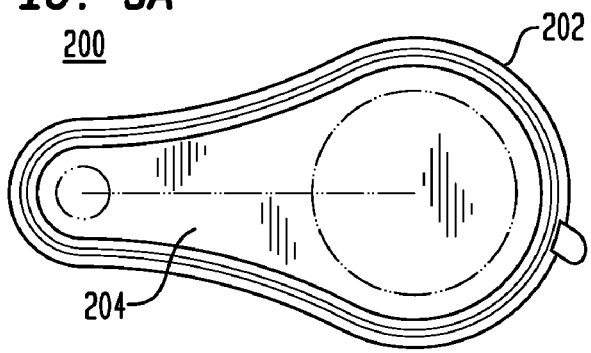
FIGS. 5A-5E show a system for aligning and positioning medical patches including a series of sequentially smaller medical patches, in accordance with one embodiment of the present invention.

Referring to FIG. 5A, in one embodiment, a medical patch system includes a first medical patch 200 having a first outer locating ring 202 and a first inner patch 204 that is connected to the first outer locating ring 202. The first inner patch 204 may be separated from the first outer locating ring 202 and removed from the first outer locating ring 202, leaving the first outer locating ring 202 bounding a central opening for aligning and positioning a second, smaller medical patch.

Figure 5B:
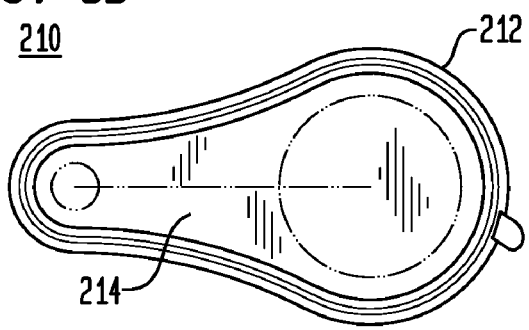

Referring to FIG. 5B, in one embodiment, a medical patch system includes a second medical patch 210 having a second outer locating ring 212 and a second inner patch 214 that is connected to the second outer locating ring 212. The second medical patch 210 is smaller than the first medical patch 200. The second outer locating ring 212 of the second medical patch 210 is preferably adhered to a region of the patient's skin that is different than the region engaged by the adhesive on the first medical patch 200.

Figure 5C:
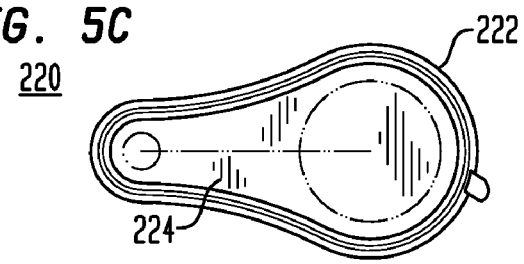

Referring to FIG. 5C, the medical patch system includes a third medical patch 230 having a third outer locating ring 222 and a third inner patch 224 that is connected to the third outer locating ring 222. The third medical patch 220 is smaller than the second medical patch 210. The third outer locating ring 222 of the third medical patch 220 is preferably adhered to a region of the patient's skin that is different than the region engaged by the adhesive on the second medical patch 210.

Figure 5D:
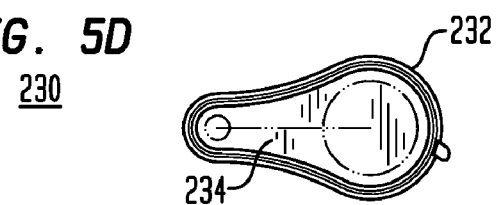
Figure 5E:
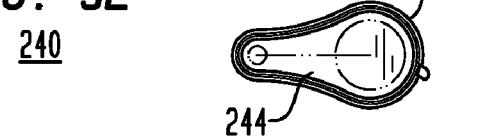

Referring to FIG. 5D, the medical patch system includes a fourth medical patch 230 having a fourth outer locating ring 232 and a fourth inner patch 234 that is connected to the fourth outer locating ring 232. The fourth medical patch 230 is smaller than the third medical patch 220. The fourth outer locating ring 232 of the fourth medical patch 230 is preferably adhered to a region of the patient's skin that is different than the region engaged by the adhesive on the third medical patch 220.

Referring to FIG. 5D, the medical patch system includes a fifth medical patch 240 having a fifth outer locating ring 242 and a fifth inner patch 244 that is connected to the fifth outer locating ring 242. The fifth medical patch 240 is smaller than the fourth medical patch 230. The fifth outer locating ring 242 of the fifth medical patch 240 is preferably adhered to a region of the patient's skin that is different than the region engaged by the adhesive on the fourth medical patch 230.

FIGS. 5A-5E show a medical patch system having a series of five sequentially smaller medical patches. In other embodiments, however, a medical patch system may have fewer or more medical patches.

In one embodiment, the medical patches disclosed herein may be positioned in an area of the body that is physically and/or visually inaccessible. For example, a medical patch may be placed on a patient's back. Thus, there is a need for medical patches having tactile sensing features that enable a patient to distinguish the various parts of the patch, even when the patch is not visible. There is also a need for tactile sensing features that make it easier for patients to remove used medical patches, and align and position replacement medical patches.

Figure 6:
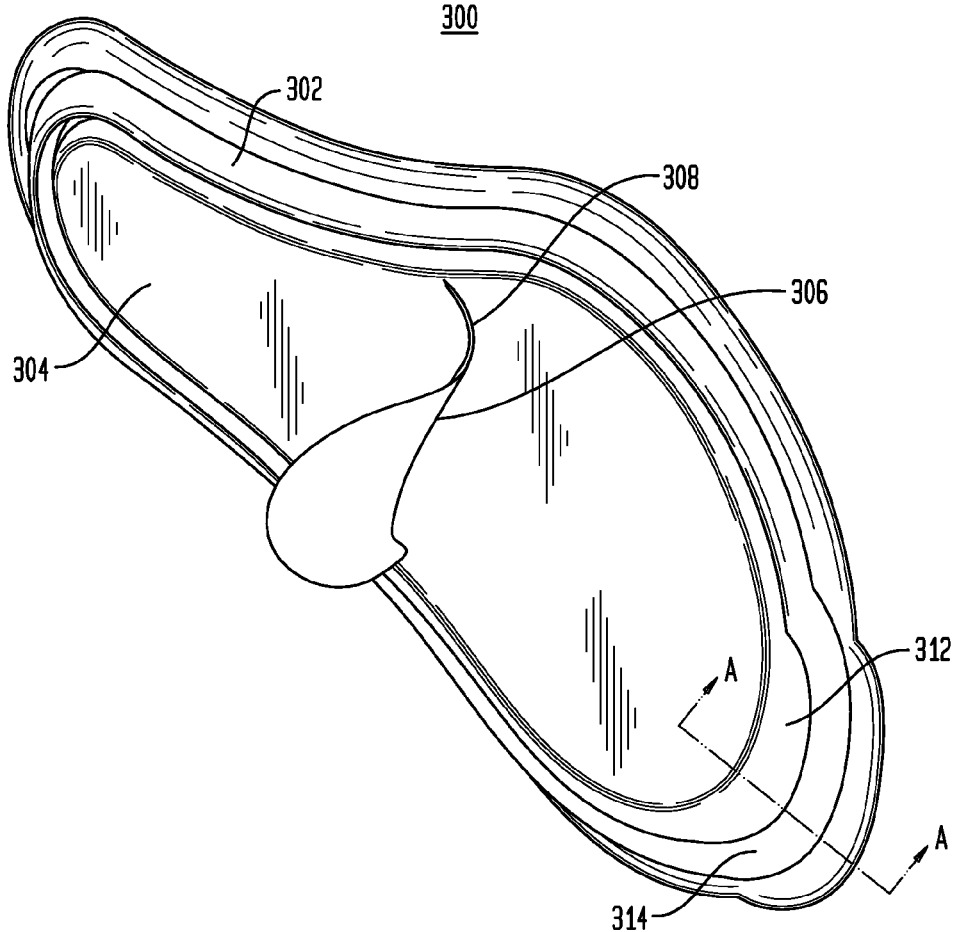
FIG. 6 shows a perspective view of a medical patch, in accordance with one embodiment of the present invention.

Referring to FIG. 6, in one embodiment, a medical patch 300 includes an outer locating ring 302 and an inner patch 304 that is secured to the outer locating ring 302. The inner patch 304 includes a flexible flap 306 that lies over a top surface of the inner patch 304. The flexible release flap 306 is preferably centered within the inner patch 304 so that it may be easily identified by a patient, even in instances where the patient cannot see the medical patch 300. The flexible release flap 306 is desirably secured to a release string 308 that extends between the inner patch 304 and the outer locating ring 302. In operation, a patient may "blindly" feel for the flexible release flap 306, and pull on the flexible release flap 306 for pulling the release string 308. The patient continues pulling the release string 308 until the inner patch 304 is separated from the outer locating ring 302. A second, smaller patch (not shown) may be aligned and positioned within the outer locating ring 302 that remains adhered to the patient.

Referring to FIG. 6, in one embodiment, the medical patch 300 includes additional tactile sensing features including a first ledge 312 extending from an outer edge of the inner patch 304, and a second ledge 314 extending from an outer edge of the outer locating ring 302. The first and second ledges 312, 314 preferably have undercuts formed therein that enable an operator to get leverage for handling and removing the various parts of the medical patch.

Figure 7:
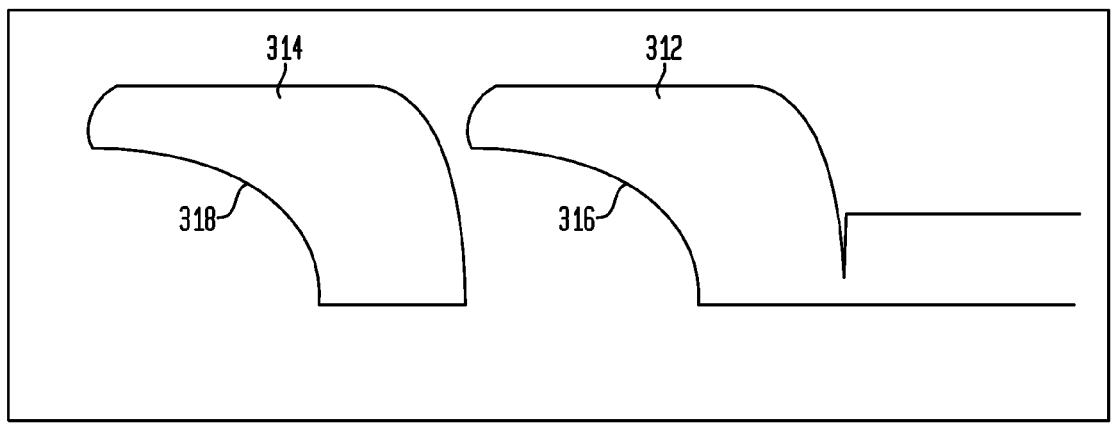
FIG. 7 shows a sectional view of the medical patch of FIG. 6 taken along line A-A of FIG. 6.

Referring to FIG. 7, in one embodiment, the first ledge 312 is offset from the second ledge 314. The first ledge 312 has an undercut 316 that enables an operator to place his or her fingers beneath the first ledge 312. The undercut 316 allows the patient to feel the first ledge and to obtain leverage for peeling the part away from the patient's skin. The second ledge 314 also includes an undercut 318 that provides tactile sensing for the patient and leverage for peeling away the outer locating ring 302 (FIG. 6) from the patient's skin.

Figure 8A:
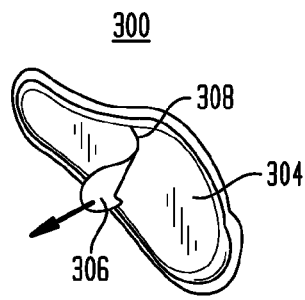
FIGS. 8A-8F show a medical patch having a pull string for separating an inner patch from an outer locating ring, in accordance with one embodiment of the present invention.
Figure 8B:
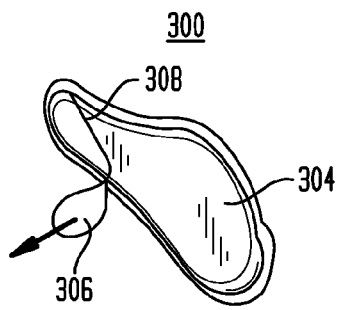
Figure 8C:
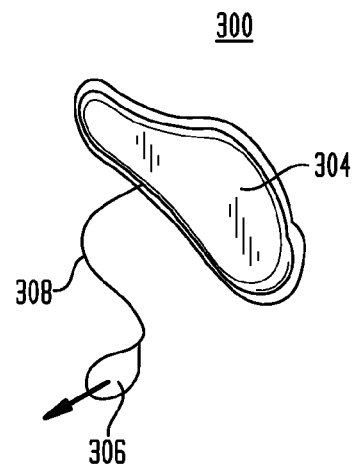
Figure 8D:
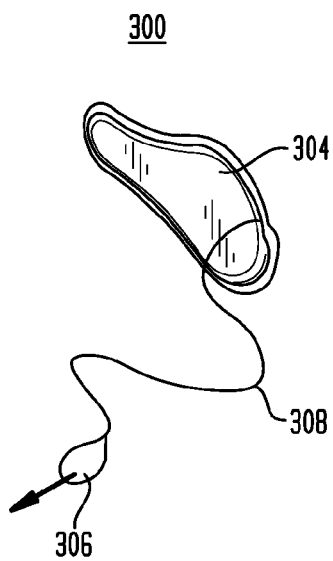
Figure 8E:
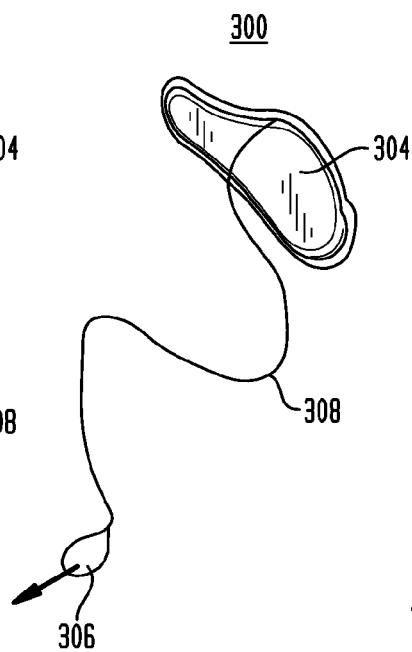
Figure 8F:
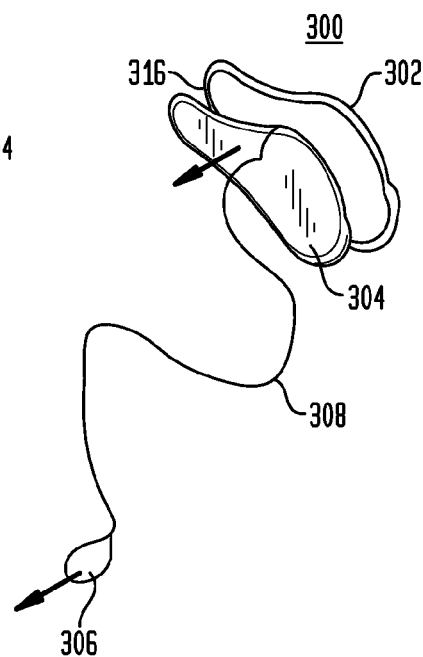

Referring to FIGS. 8A-8F, in one embodiment, the delivery patch 300 includes a flexible release flap 306 that enables an operator to use tactile sensing for replacing medical patches. Referring to FIGS. 8A-8F, the flexible release flap 306 is connected to string 308 that extends between the inner patch 304 and the outer locating ring 302. As shown in FIGS. 8B-8F, as the flexible flap 306 is pulled, the string 308 is also pulled for separating the inner patch 304 from the outer locating ring 302. Referring to FIG. 8F, once the inner patch 304 is removed, an inner edge 316 of the outer locating ring 302 may be used to align and position a second medical patch within a central opening 318 in the outer locating ring 302.

Figure 9:
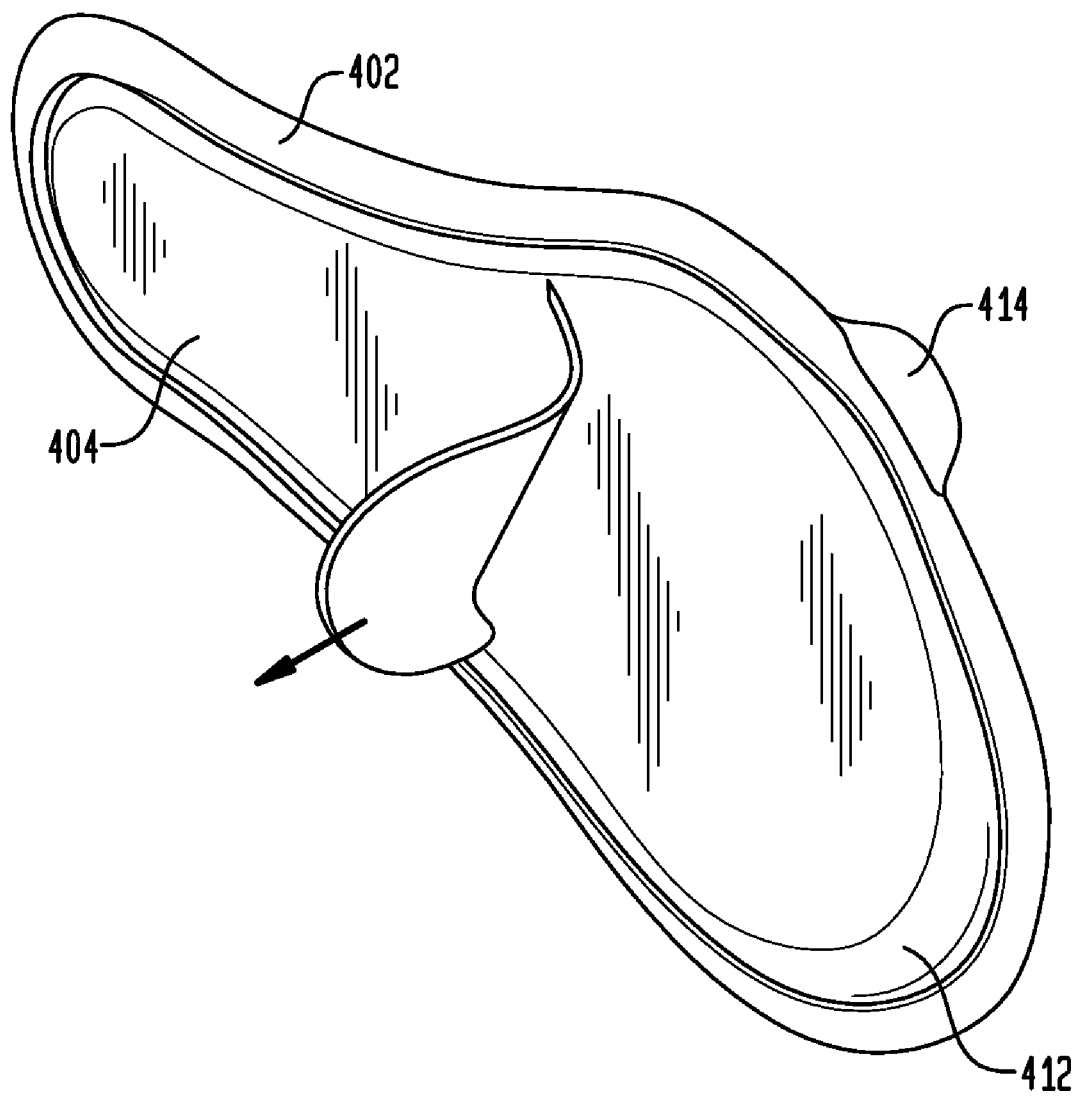
FIG. 9 shows a medical patch having tactile sensing elements, in accordance with another embodiment of the present invention.

Referring to FIG. 9, a delivery patch 400 includes an outer locating ring 402 and an inner patch 404 that is connected with the outer locating ring. The inner patch 404 has a first ledge 412 that is preferably similar in structure as the first ledge 312 shown in FIGS. 6 and 7. The outer locating ring 402 has a second ledge 414 that is preferably similar in structure as the second ledge 314 shown in FIGS. 6 and 7. The first and second ledges 412, 414 are not aligned with one another, providing an additional tactile sensing feature for distinguishing between different medical patches or different parts of a medical patch.

Figure 10A:
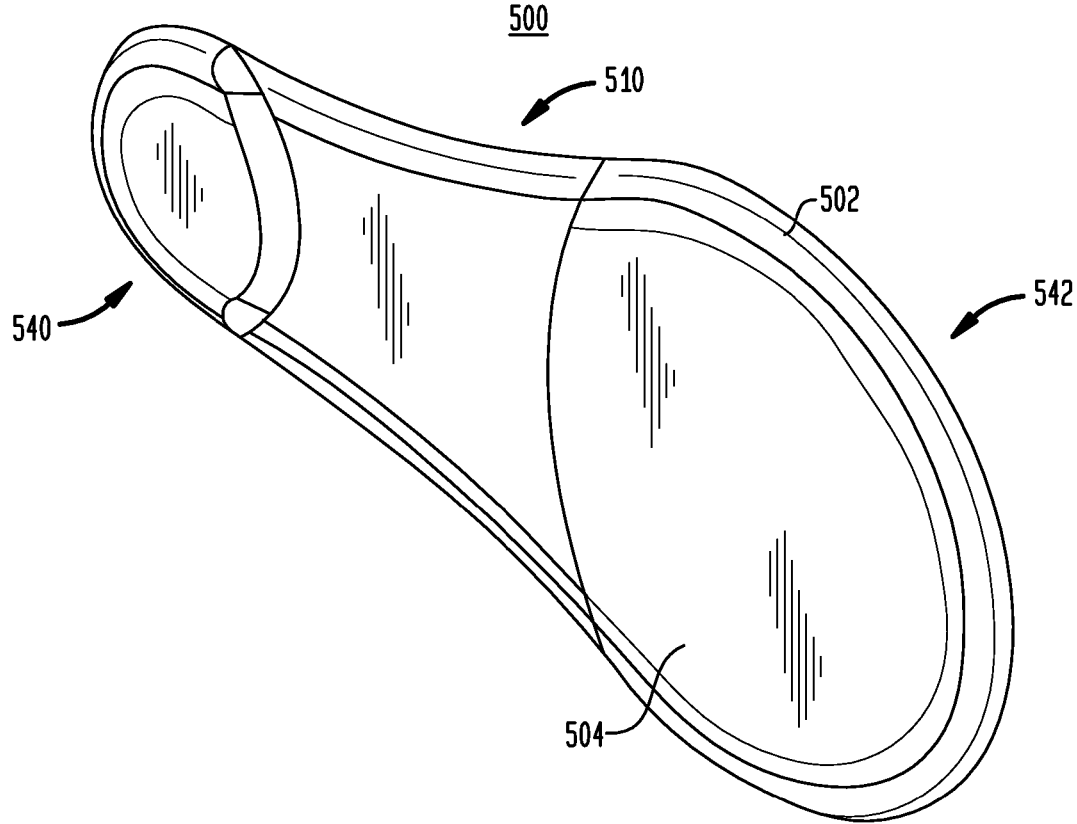
FIGS. 10A and 10B show a medical patch having a more flexible section, in accordance with one embodiment of the present invention.
Figure 10B:
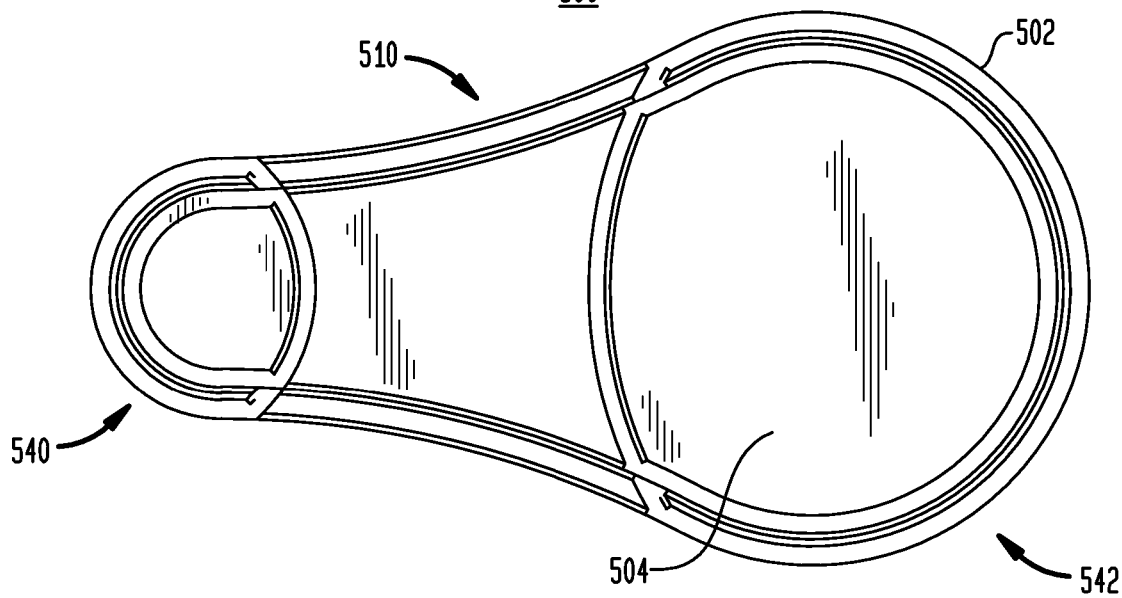

Referring to FIGS. 10A and 10B, in one embodiment, a medical patch 500 includes an outer locating ring 502 and an inner patch 504 that is bounded by the outer locating ring 502. The outer locating ring 502 and the inner patch 504 are preferably attached to one another as described above, and may be separated from one another using the structures and techniques disclosed herein. The medical patch 500 preferably includes a central section 510 that is thinner than the respective end sections 540, 542 of the medical patch 500. The thinner central section 510 improves and/or enhances the flexibility of the patch at desired locations. The particular embodiment shown in FIGS. 10A and 10B provides a medical patch 500 having a thinner central section for enhancing flexibility. In other embodiments, the thinner section can be provided at any location on the patch to enhance flexibility of a medical patch for a particular purpose. The particular location of the thinner section may change depending upon the body part to which the delivery patch is attached. For one use (e.g. placement on a back), the patch has flexibility in a first section. For another use, it may be desirable to provide a patch having flexibility in an entirely different section for optimizing performance for that particular purpose.

Figure 11A:
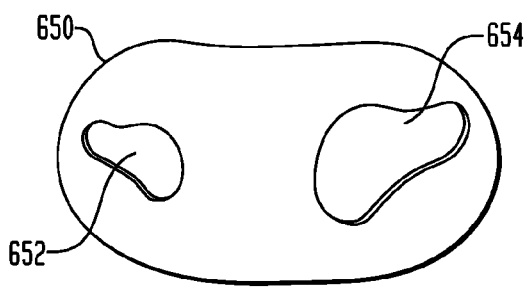
FIGS. 11A-11F show a system including a template for locating medical patches on opposite sides of a body, in accordance with one embodiment of the present invention.

In one embodiment, it may be desirable to position medical patches on opposite sides of a patient's body. In one embodiment, it may be desirable to position patches on opposite sides of the sacral region of the back. Referring to FIG. 11A, in one embodiment, a system for positioning medical patches includes a template 650 having a first cutout 652 sized to receive a first medical patch having a first size, and a second cutout 654 sized to receive a second medical patch that is larger than the first medical patch. In one embodiment, the medical patches may be the same size. In one embodiment, the template preferably includes an adhesive for securing the template to a surface.

Figure 11B:
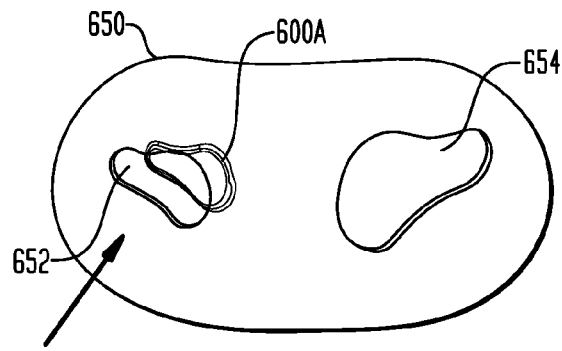
Figure 11C:
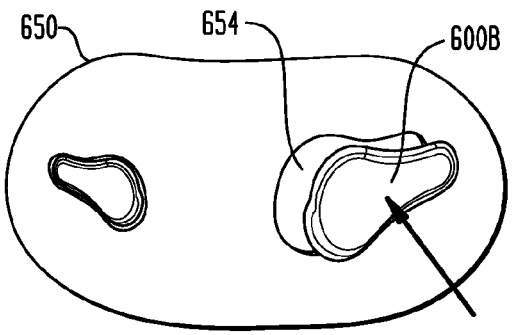

Referring to FIG. 11B, in one embodiment, a first medical patch 600A is adhered to a patient's back. The first cutout 652 on the template 650 is aligned over the medical patch 600A. Referring to FIGS. 11B and 11C, as the first cutout 652 of the template 650 is aligned with the first medical patch 600A, the second cutout 654 is properly aligned over a second region of the patient's back. Referring to FIG. 11C, the second cutout 654 provides alignment for a second medical patch 600B. The larger second medical patch 600B is preferably positioned within the second cutout 654 of the template 650 and adhered to the patient's skin.

Figure 11D:
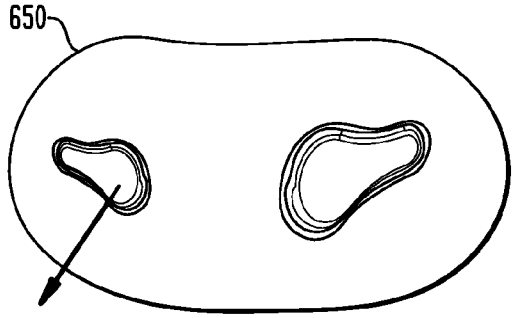
Figure 11E:
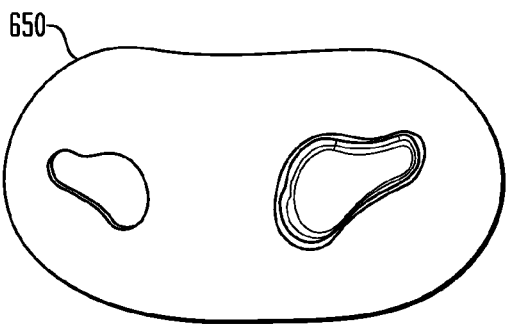
Figure 11F:
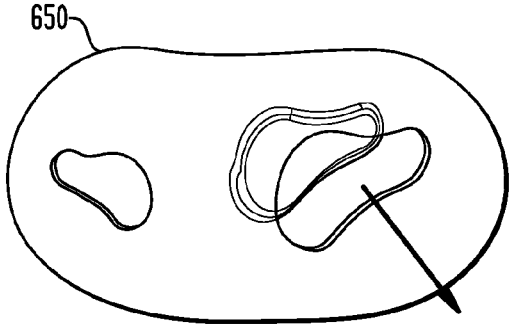

Referring to FIG. 11D, after the second medical patch 600B is attached to the patient's skin, the first medical patch 600A may be peeled away from the patient's skin. FIG. 11E shows the template 650 after the first medical patch 600A has been removed from the first cutout 652. Referring to FIG. 11F, with the larger second medical patch 600B now properly aligned over and adhered to the patient's skin, the template 650 may be removed. After a period of time, one or more sequentially smaller medical patches may be positioned over the location covered by the second medical patch 600B. Proper alignment of the subsequently smaller medical patches may be aligned using the techniques shown and described above in FIGS. 2A-2F, 3A-3F and 4A-4I.

Figure 12:
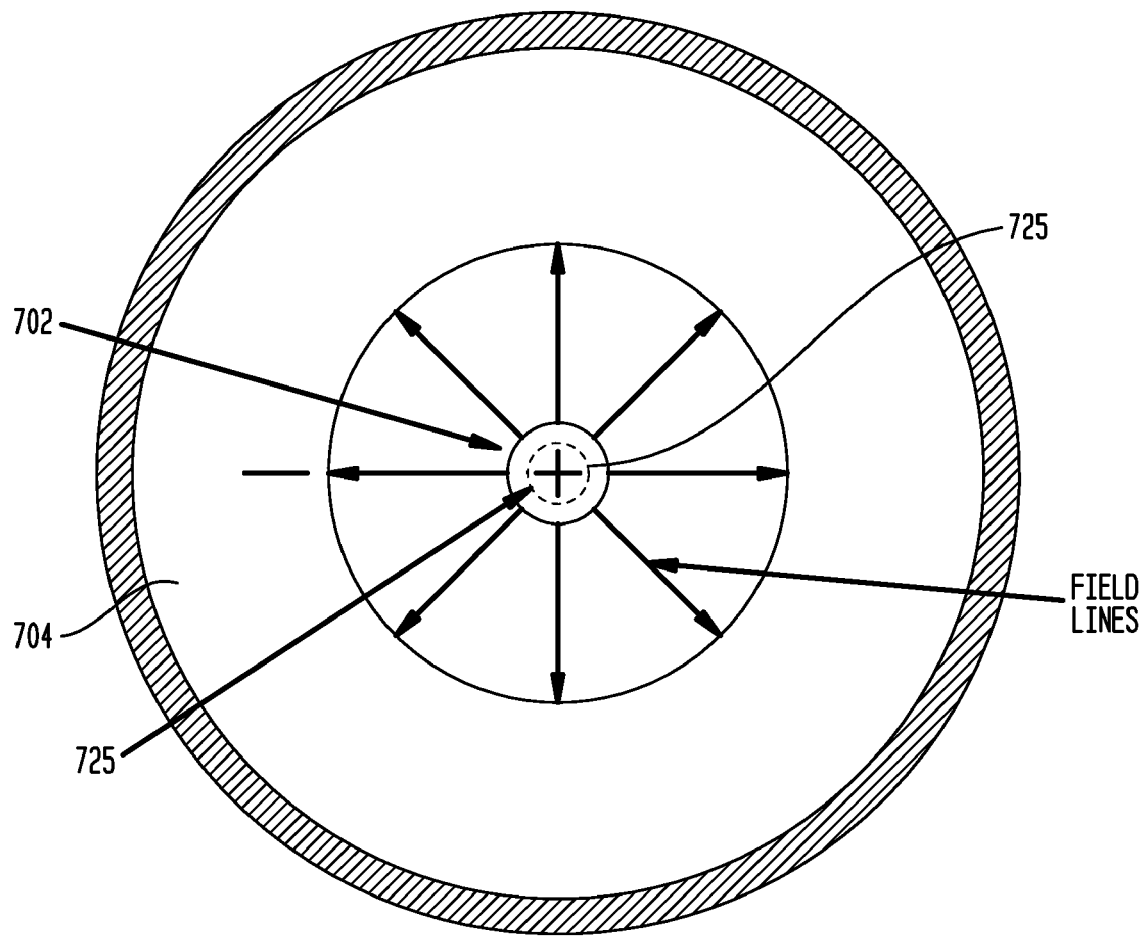
FIG. 12 shows a bottom plan view of a medical patch including a central alignment opening, in accordance with one embodiment of the present invention.

Referring to FIG. 12, in one embodiment, a medical patch 700, such as a concentric skin electrode patch, includes a cathode 702, a cathode 704, and a central opening 725 for positioning the medical patch over a skin tattoo or ink marking on the patient's skin. The medical patch 700 includes an adhesive layer 735 for securing the medical patch 700 to the patient's skin. The central opening 725 helps medical personnel or the patient precisely position one or more medical patches over a target location on a patient.

Figure 13A:
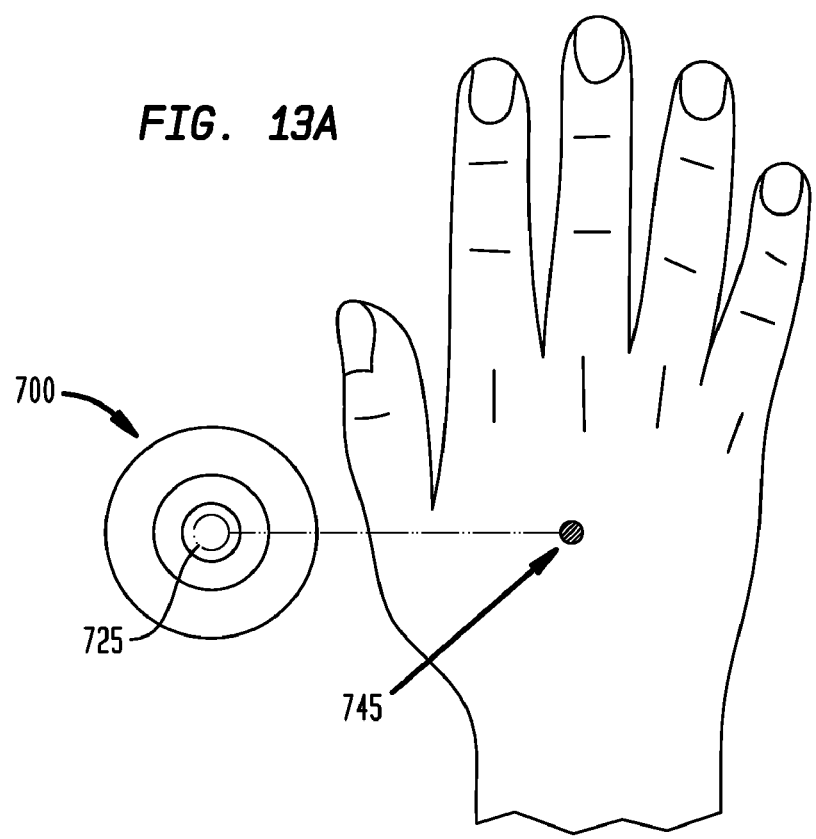
FIGS. 13A-13B show a method of aligning and positioning the medical patch of FIG. 12 over a target location on a patient, in accordance with one embodiment of the present invention.
Figure 13B:
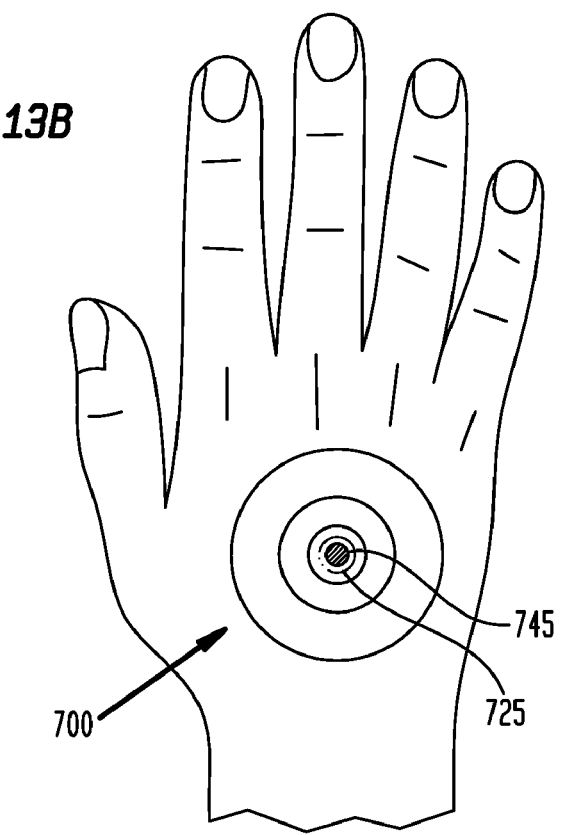

FIGS. 13A and 13B illustrate placement of the medical patch 700 over a skin tattoo or ink marking 745 on the patient's skin by aligning the central opening 725 of the patch with the tattoo 745. Referring to FIG. 13B, the central opening 725 of the medical patch 700 is aligned over the skin tattoo or marking 745 so that the marking is aligned with and viewable through the central opening. The adhesive on the underside of the medical patch 700 faces toward the skin for securing the medical patch to the skin.

Figure 14A:
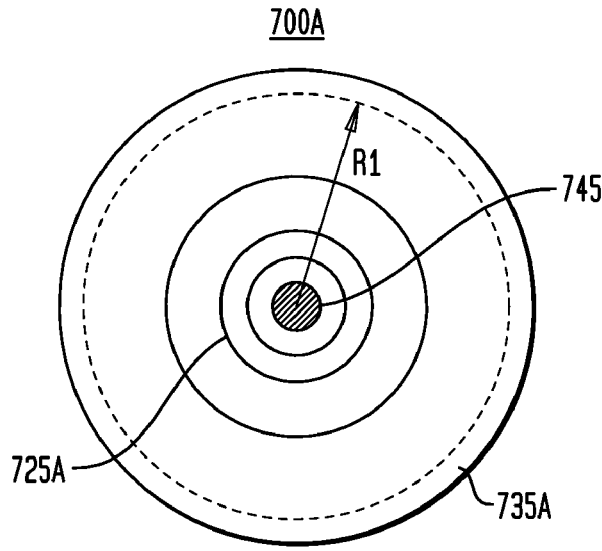
FIGS. 14A-14C show a system including a series of medical patches having smaller diameters, in accordance with one embodiment of the present invention.
Figure 14B:
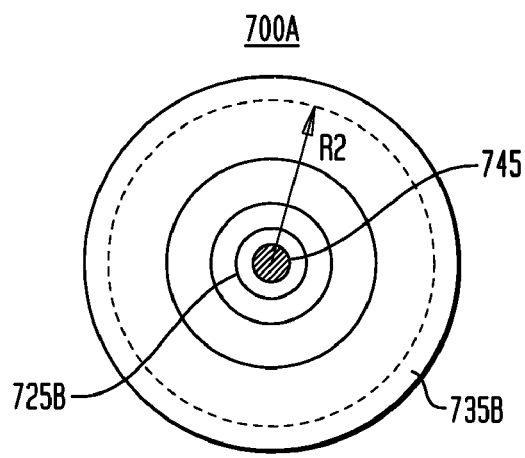
Figure 14C:
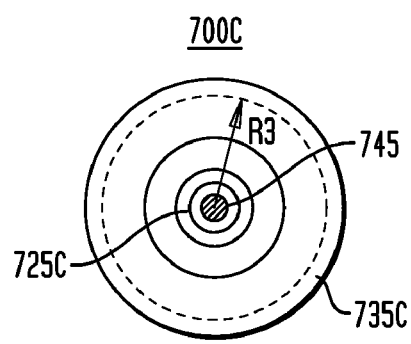

Referring to FIGS. 14A-14C, a self-locating medical patch system includes a plurality of medical patches 700A-700C having different sizes. Referring to FIG. 14A, a first medical patch 700A has a central opening 725A for aligning the patch over a skin tattoo 745. The first medical patch 700A has an adhesive layer 735A spaced a distance $R_1$ from the central opening 725A of the patch. Referring to FIG. 14B, a second medical patch 700B has a central opening 725B for aligning the patch over the skin tattoo 745 shown in FIG. 14B. The second medical patch 700B has an adhesive layer 735B spaced a distance $R_2$ from the central opening 725B of the patch. Referring to FIG. 14C, a third medical patch 700C has a central opening 725C for aligning the patch over the skin tattoo 745 shown in FIGS. 14A and 14B. The third medical patch 700C has an adhesive layer 735C spaced a distance $R_3$ from the central opening 725C of the third patch. The adhesive layers 735A, 735B and 735C of the respective medical patches have different radii for ensuring that the adhesive layers engage different areas of the skin for minimizing the likelihood of skin irritation.

In the embodiment shown in FIGS. 14A-14C, the medical patches have different sizes, so that the adhesive layers placed adjacent the perimeters of the respective patches have different radii. In another embodiment, however, the medical patches may have the same size and the spacing of the adhesive from the central openings may change.

Figure 15A:
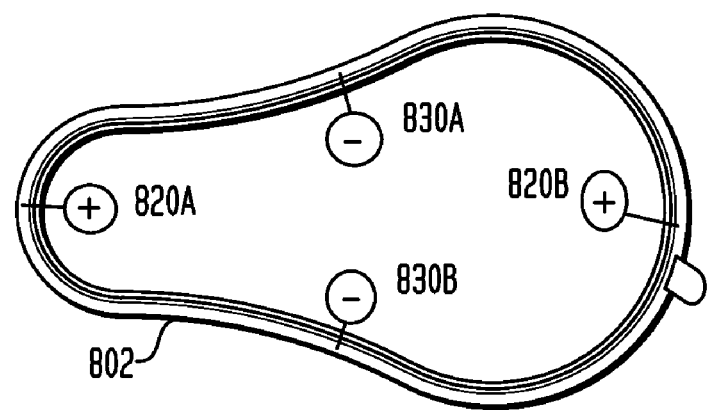
FIGS. 15A-15B show a medical patch system including medical patches having magnets incorporated therein for guiding alignment of replacement patches, in accordance with one embodiment of the present invention.
Figure 15B:
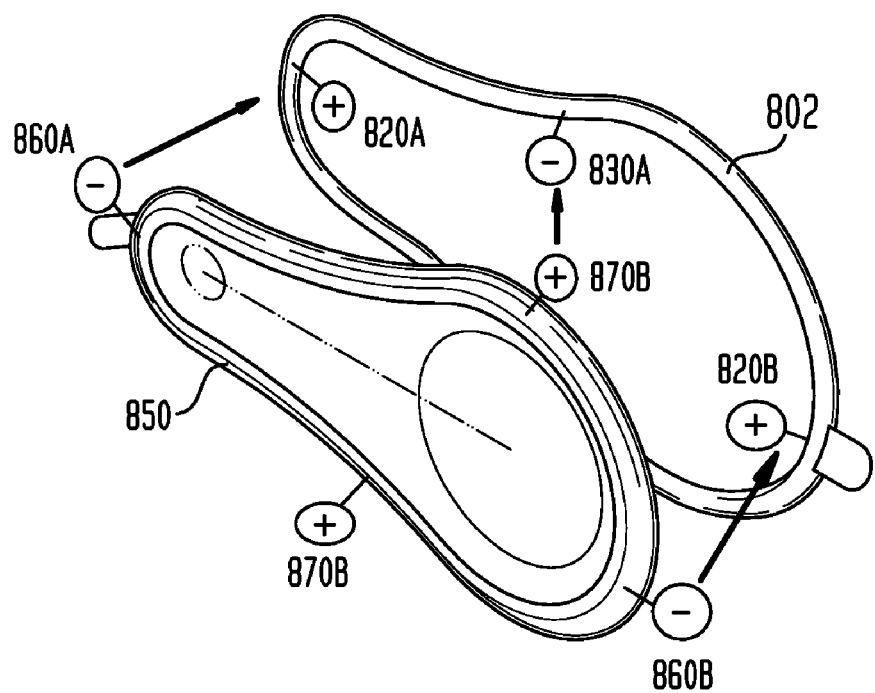

In one embodiment, magnets may be incorporated into the respective medical patches for generating magnetic fields used to guide alignment and positioning of replacement medical patches. Referring to FIGS. 15A and 15B, in one embodiment, a medical patch system includes magnets coupled with medical patches for guiding precise alignment and positioning of replacement medical patches over a target location. In one embodiment, the magnets may be embedded within portions of the medical patches. Referring to FIG. 15A, an outer locating ring 802 of a first medical patch includes positively charged magnets 820A, 820B incorporated into the respective ends of the outer locating ring, and negatively charged magnets 830A, 830B incorporated into the respective sides of the outer locating ring. Referring to FIG. 15B, the medical patch system includes a second medical patch 850 that is adapted to be positioned within a central opening of the outer locating ring 802. The second medical patch 850 includes negatively charged magnets 860A, 860B incorporated into the respective ends thereof, and positively charged magnets 870A, 870B incorporated into the respective sides thereof. As the second medical patch 850 is inserted into the central opening of the outer locating ring 802, the oppositely charged magnets generate a magnetic attraction that guides alignment of the second medical patch 850 relative to the outer locating ring 802.

As used herein, the terminology "target location" may mean a precise location on a surface, such as a skin surface of a patient. The terminology "target location" may also mean a precise location or area under a surface, such as a single nerve or a group of nerves located under a skin surface. In one embodiment, the terminology "target location" may cover a larger area such as a sacral region of a patient's back. For example, the medical patch system of the present invention may be used for treating an overactive bladder, and the medical patches may first be used over the sacral region on the left side of a patient's spine and then used over the same sacral region on the right side of a patient's spine. The present invention contemplates that the alignment features disclosed herein will facilitate precise placement of the replacement patches, and that moving patches from the left side to the right side of the spine will be considered to treat the same "target location."

In one embodiment, a medical patch or a series of medical patches are adapted for stimulating a target nerve or a bundle of nerves using the devices and techniques described in commonly assigned United States Patent Application Publication Nos. U.S. 2005/0277998 (U.S. application Ser. No. 11/146,522, filed Jun. 7, 2005), U.S. 2006/0195153 (U.S. application Ser. No. 11/343,627, filed Jan. 31, 2006), U.S. 2006/0195146 (U.S. application Ser. No. 11/344,285, filed Jan. 31, 2006), and U.S. 2007/0185541 (U.S. application Ser. No. 11/497,861, filed Aug. 2, 2006), the disclosures of which are hereby incorporated by reference herein. In one embodiment of the medical patch, the waveform is desirably generated by modulating a carrier waveform with a pulse envelope. Properties of the carrier waveform such as amplitude, frequency, and the like, are chosen so as to overcome the tissue impedance and the stimulation threshold of the target nerve.

The headings used herein are for organizational purposes only and are not meant to limit the scope of the description or the claims. As used throughout this application, the word "may" is used in a permissive sense (i.e., meaning having the potential to), rather than the mandatory sense (i.e., meaning must). Similarly, the words "include", "including", and "includes" mean including but not limited to. To facilitate understanding, like reference numerals have been used, where possible, to designate like elements common to the figures.

While the foregoing is directed to embodiments of the present invention, other and further embodiments of the invention may be devised without departing from the basic scope thereof. As such, the scope of the present invention is to be limited only as set forth in the appended claims.

What is claimed is:

1. A medical patch system comprising: a first medical patch including a first outer locating ring securable to a surface and a first inner patch disposed within a first central area bounded by said first outer locating ring, said first inner patch being connected to but separable from said first outer locating ring; a second medical patch adapted for insertion into said first central area bounded by said first outer locating ring after said first inner patch is separated from said first outer locating ring; and wherein the second medical patch includes a second outer locating ring securable to the surface and adapted for insertion into said first central area bounded by said first outer locating ring.

2. The medical patch system as claimed in claim 1, wherein said second medical patch further comprises: a second inner patch disposed within a second central area bounded by said second outer locating ring, said second inner patch being separable from said second outer locating ring.

3. The medical patch system as claimed in claim 2, wherein said first outer locating ring is adapted for removal from the surface after said second outer locating ring is secured to the surface.

4. The medical patch system as claimed in claim 1, wherein said first outer locating ring includes an alignment surface for guiding alignment and orientation of said second medical patch relative to said first outer locating ring.

5. The medical patch system as claimed in claim 2, wherein said first outer locating ring includes a first adhesive for securing said first outer locating ring to the surface and said second outer locating ring includes a second adhesive for securing said second outer locating ring to the surface, and wherein said second adhesive has a different size, shape or pattern than said first adhesive.

6. The medical patch system as claimed in claim 2, further comprising a third medical patch adapted for insertion into the second central area bounded by said second outer locating ring after said second inner patch is separated from said second outer locating ring, and wherein said second outer locating ring of said second medical patch includes an alignment surface for guiding alignment and orientation of said third medical patch relative to said second outer locating ring.

7. The medical patch system as claimed in claim 6, wherein said third medical patch comprises: a third outer locating ring securable to the surface; a third inner patch disposed within a third central area bounded by said second outer locating ring, said third inner patch being separable from said third outer locating ring.

8. The medical patch system as claimed in claim 2, wherein each said medical patch has an active region that is adapted to deliver neurostimulation, pain-management, agents, hormones, or pharmacological agents to a target location of a patient, 9. The medical patch system as claimed in claim 8, wherein said outer locating rings have alignment structure incorporated therein for ensuring precise alignment of said active regions of said medical patches over the target location.

10. The medical patch system as claimed in claim 9, wherein said alignment structure comprises at least one magnet coupled with each of said outer locating rings.

11. The medical patch system as claimed in claim 2, wherein said outer locating rings have irregular shapes that enable said outer locating rings to be assembled together in only one configuration.

12. The medical patch system as claimed in claim 2, wherein each said medical patch includes a release extending between said inner patch and said outer locating ring that is selectively engaged for separating said inner patch from said outer locating ring.

13. The medical patch system as claimed in claim 2, wherein at least one of said medical patches has at least one tactile identifier incorporated therein for distinguishing said medical patches from one another or for identifying different parts of said at least one of said medical patches.

14. The medical patch system as claimed in claim 13, wherein said at least one tactile identifier comprises a ledge extending outwardly from an outer edge of at least one of said outer locating rings.

15. The medical patch system as claimed in claim 14, wherein said second medical patch is inserted into said first central area bounded by said first outer locating ring and a first edge on said first outer locating ring is offset from a second edge on said second outer locating ring.

16. A medical patch system comprising: at least two medical patches adapted to be secured in series over a target location; said at least two medical patches including a first medical patch having a first outer alignment part and a first inner part bounded by said first outer alignment part, wherein said first inner part has an active region that delivers a therapeutic benefit to the target location, and wherein said first inner part is connected to but separable from said first outer alignment part for being replaced by a second medical patch; said second medical patch being securable over the target location after said first inner part of said first patch has been separated from said first outer alignment part of said first medical patch for delivering a therapeutic benefit to the target location, wherein the second medical patch includes a second outer alignment part adapted for insertion into a central area bounded by the first outer alignment part, wherein alignment and positioning of said second medical patch over the target location is guided by said first outer alignment part of said first medical patch.

17. The medical patch system as claimed in claim 16, wherein said second medical patch further comprises: a second inner part bounded by said second outer alignment part, wherein said second inner part includes an active region that delivers the therapeutic benefit to the target location, and wherein said first and second outer alignment parts comprise adhesive for securing said medical patches to a surface over the target location.

18. the medical patch as claimed in claim 17, wherein said first and second outer alignment parts have irregular shapes that generally conform to one another for ensuring alignment of the active region of said second inner part over the target location.

19. The medical patch as claimed in claim 17, wherein each said outer alignment part includes at least one magnet for aligning adjacent outer alignment parts relative to one another.

20. The medical patch system as claimed in claim 17, further comprising a third medical patch adapted for insertion into an area bounded by said second outer alignment part after said second inner part is separated from said second outer alignment part.

21. A medical patch system comprising: a plurality of replaceable medical patches adapted to be secured in series over a target location to provide therapeutic benefit to the target location; at least one of said medical patches including an alignment element for guiding proper alignment and orientation of a replacement medical patch over the target location; each said medical patch including an adhesive for securing said medical patches over the target location, wherein said adhesive on at least two of said medical patches has different sizes, shapes, or patterns; each said medical patch further includes an outer locating ring adapted for insertion into a central area bounded by a previously secured medical patch.

22. The medical patch as claimed in claim 21, wherein each said medical patch further includes an inner patch connected to but separable from said outer locating ring, wherein each said inner patch includes an active region adapted to deliver the therapeutic benefit to the target location.

23. The medical patch system as claimed in claim 21, wherein said plurality of medical patches are smaller in series so that a first medical patch is replaceable by a smaller second medical patch.

24. The medical patch system as claimed in claim 21, wherein said plurality of medical patches are larger in series so that a first medical patch is replaceable by at least one larger medical patch.

25. The medical patch system as claimed in claim 21, wherein at least one of said medical patches has a first region that is more flexible and a second region that is less flexible.

* * * * *